(12) United States Patent
Goodrich, Jr. et al.

(10) Patent No.: US 6,258,577 B1
(45) Date of Patent: *Jul. 10, 2001

(54) METHOD AND APPARATUS FOR INACTIVATION OF BIOLOGICAL CONTAMINANTS USING ENDOGENOUS ALLOXAZINE OR ISOALLOXAZINE PHOTOSENSITIZERS

(75) Inventors: Raymond Paul Goodrich, Jr., Denver; Frank Corbin, III, Littleton; Edward C. Wood, Jr., Lakewood, all of CO (US)

(73) Assignee: Gambro, Inc., Lakewood, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,666

(22) Filed: Jul. 21, 1998

(51) Int. Cl.⁷ .............................. C12N 13/00; A01N 1/02
(52) U.S. Cl. ........................ 435/173.3; 435/2; 435/173.1
(58) Field of Search .......................... 435/2, 173.3, 173.1

(56) References Cited

U.S. PATENT DOCUMENTS

| | | | |
|---|---|---|---|
| Re. 32,874 | 2/1989 | Rock et al. | 424/101 |
| 683,690 | 10/1901 | Johnson | 604/20 |
| 1,733,239 | 10/1929 | Roberts | 607/93 |
| 1,961,700 | 6/1934 | Moehler | 250/455.11 |
| 2,056,614 | 10/1936 | Moehler | 250/453.11 |
| 2,212,230 | 8/1940 | Goldmann | 342/415 |
| 2,212,330 | 8/1940 | Thomas | 250/453.11 |
| 2,340,890 | 2/1944 | Lang et al. | 250/429 |
| 3,456,053 | 7/1969 | Crawford | 424/220.1 |
| 3,683,177 | 8/1972 | Veloz | 250/435 |
| 3,683,183 | 8/1972 | Vizzini et al. | 250/435 |
| 3,705,985 | 12/1972 | Manning et al. | 250/435 |
| 3,776,694 | 12/1973 | Leittl | 422/24 |
| 3,852,032 | 12/1974 | Urbach | 422/24 |
| 3,864,081 | 2/1975 | Logrippo | 250/435 |
| 3,894,236 | 7/1975 | Hazelrigg | 250/435 |
| 3,926,556 | 12/1975 | Boucher | 422/21 |
| 3,927,325 | 12/1975 | Hungate et al. | 250/435 |
| 4,124,598 | 11/1978 | Hearst et al. | 549/282 |
| 4,139,348 | 2/1979 | Swartz | 549/282 |
| 4,169,204 | 9/1979 | Hearst et al. | 546/283.1 |
| 4,181,128 | 1/1980 | Swartz | 604/20 |
| 4,196,281 | 4/1980 | Hearst et al. | 536/24.31 |
| 4,312,883 | 1/1982 | Baccichetti et al. | 514/455 |
| 4,321,918 | 3/1982 | Clark, II | 604/4 |

(List continued on next page.)

FOREIGN PATENT DOCUMENTS

| | | |
|---|---|---|
| 0 066 886 | 6/1982 | (EP) . |
| 0 124 363 | 4/1984 | (EP) . |
| 0 196 515 A1 | 3/1986 | (EP) . |
| 0 525 138 B1 | 12/1991 | (EP) . |
| 0 801 072 A2 | 3/1997 | (EP) . |
| 2674753 | 10/1992 | (FR) . |
| 2715303 | 7/1995 | (FR) . |
| 2718353 | 10/1995 | (FR) . |
| WO 89/06702 | 7/1989 | (WO) . |
| WO 91/02529 | 3/1991 | (WO) . |
| WO 92/11057 | 7/1992 | (WO) ........................... A61M/37/00 |
| WO 92/17173 | 10/1992 | (WO) . |
| WO 94/07426 | 4/1994 | (WO) ........................... A61B/19/00 |
| WO 94/07499 | 4/1994 | (WO) . |
| WO 95/02325 | 1/1995 | (WO) ............................. A01N/1/02 |
| WO 95/11028 | 4/1995 | (WO) . |
| WO 95/12973 | 5/1995 | (WO) . |
| WO 95/16348 | 6/1995 | (WO) . |
| WO 96/14740 | 5/1996 | (WO) . |
| WO 97/07674 | 3/1997 | (WO) . |
| WO 97/22245 | 6/1997 | (WO) . |
| WO 97/36581 | 10/1997 | (WO) . |
| WO 97/36634 | 10/1997 | (WO) . |
| WO 98/31219 | 7/1998 | (WO) ............................. A01N/1/02 |
| WO 99/11305 | 3/1999 | (WO) . |

OTHER PUBLICATIONS

Friedman, L.I. et al., "Reducing the infectivity of blood components—what we have learned," (1995) *Immunological Investigations* 24(1&2):49–71.

Ghiron, C.A. and Spikes, J.D., "The flavin–sensitized photoinactivation of trypsin," (1965) *Photochemistry and Photobiology* 4:13–26.

Hoffmann, M.E. and Meneghini, R., "DNA strand breaks in mammalian cells exposed to light in the presence of riboflavin and tryptophan," (1979) *Photochemistry and Photobiology* 29:299–303.

(List continued on next page.)

*Primary Examiner*—Jon P. Weber
(74) *Attorney, Agent, or Firm*—Greenlee, Winner and Sullivan, P.C.

(57) ABSTRACT

Methods and apparatuses are provided for inactivation of microorganisms in a fluid containing blood or blood products and comprising biologically active proteins. The method includes the steps of adding an effective, non-toxic amount of an endogenous photosensitizer to the fluid; exposing the fluid to photoradiation sufficient to activate the endogenous photosensitizer; and allowing the activated endogenous photosensitizer to interfere with nucleic acid present in microorganisms in the fluid so that the microorganisms are inactivated. Isoalloxazines and K- and L-vitamins are among the preferred photosensitizers. Systems and apparatuses are also provided for decontamination of such fluids using photosensitizers which include means for adding photosensitizer to the fluid; a photopermeable container for exposing the fluid to an amount of photoradiation sufficient to activate the photosensitizer; and a photoradiation source, preferably comprising a light guide, for providing sufficient photoradiation of a type and amount selected to activate the photosensitizer. Means for controlling photosensitizer concentration in the fluid and rate of fluid flow through the container, including computer processors may be included in such systems.

18 Claims, 7 Drawing Sheets

U.S. PATENT DOCUMENTS

| | | | |
|---|---|---|---|
| 4,321,919 | 3/1982 | Edelson | 604/6 |
| 4,336,809 | 6/1982 | Clark | 604/478 |
| 4,398,031 | 8/1983 | Bender et al. | 549/282 |
| 4,398,906 | 8/1983 | Edelson | 604/6 |
| 4,402,318 | 9/1983 | Swartz | 604/20 |
| 4,407,282 | 10/1983 | Swartz | 604/20 |
| 4,421,987 | 12/1983 | Herold | 250/492.1 |
| 4,424,201 | 1/1984 | Valinsky et al. | 435/34 |
| 4,428,744 | 1/1984 | Edelson | 604/6 |
| 4,456,512 | 6/1984 | Bieler et al. | 204/157.65 |
| 4,464,166 | 8/1984 | Edelson | 604/6 |
| 4,467,206 | 8/1984 | Taylor et al. | 250/435 |
| 4,474,153 | 10/1984 | Rock et al. | |
| 4,481,167 | 11/1984 | Ginter et al. | 422/29 |
| 4,493,981 | 1/1985 | Payne | 219/450 |
| 4,568,328 | 2/1986 | King | 604/6 |
| 4,573,960 | 3/1986 | Goss | 604/6 |
| 4,573,961 | 3/1986 | King | 604/6 |
| 4,573,962 | 3/1986 | Troutner | 604/6 |
| 4,576,143 | 3/1986 | Clark, III | 600/1 |
| 4,578,056 | 3/1986 | King et al. | 604/6 |
| 4,596,547 | 6/1986 | Troutner | 604/4 |
| 4,604,356 | 8/1986 | Blake, II | 435/194 |
| 4,608,255 | 8/1986 | Kahn et al. | 424/532 |
| 4,612,007 | 9/1986 | Edelson | 604/5 |
| 4,613,322 | 9/1986 | Edelson | 604/6 |
| 4,614,190 | 9/1986 | Stanco et al. | 607/88 |
| 4,623,328 | 11/1986 | Hartranft | 604/4 |
| 4,642,171 | 2/1987 | Sekine et al. | 156/345 |
| 4,645,649 | 2/1987 | Nagao | 422/186.3 |
| 4,648,992 | 3/1987 | Graf et al. | 540/124 |
| 4,649,151 | 3/1987 | Dougherty et al. | 514/410 |
| 4,651,739 | 3/1987 | Oseroff et al. | 607/88 |
| 4,683,195 | 7/1987 | Mullis et al. | 435/6 |
| 4,683,202 | 7/1987 | Mullis | 435/91.2 |
| 4,683,889 | 8/1987 | Edelson | 607/92 |
| 4,684,521 | 8/1987 | Edelson | 424/529 |
| 4,693,981 | 9/1987 | Wiesehahn et al. | 435/238 |
| 4,695,460 | 9/1987 | Holme | 424/101 |
| 4,708,715 | 11/1987 | Troutner et al. | 604/6 |
| 4,726,949 | 2/1988 | Miripol et al. | 424/534 |
| 4,727,027 | 2/1988 | Wiesehahn et al. | 435/173.2 |
| 4,737,140 | 4/1988 | Lee et al. | 604/4 |
| 4,748,120 | 5/1988 | Wiesehahn | 435/173.3 |
| 4,775,625 | 10/1988 | Sieber | 435/238 |
| 4,788,038 | 11/1988 | Matsunaga | 422/22 |
| 4,831,268 | 5/1989 | Fisch et al. | 250/432 R |
| 4,833,165 | 5/1989 | Louderback | 514/694 |
| 4,861,704 | 8/1989 | Reemtsma et al. | 435/1.1 |
| 4,866,282 | 9/1989 | Miripol et al. | 250/455.1 |
| 4,878,891 | 11/1989 | Judy et al. | 604/5 |
| 4,880,788 | 11/1989 | Moake et al. | 514/150 |
| 4,915,683 | 4/1990 | Sieber | 604/4 |
| 4,921,473 | 5/1990 | Lee et al. | 494/27 |
| 4,930,516 | 6/1990 | Alfano et al. | 128/665 |
| 4,946,438 | 8/1990 | Reemtsma et al. | 604/53 |
| 4,948,980 | 8/1990 | Wedekamp | 250/455.1 |
| 4,950,665 | 8/1990 | Floyd | 514/222.8 |
| 4,952,812 | 8/1990 | Miripol et al. | 250/455.1 |
| 4,960,408 | 10/1990 | Klainer et al. | 604/4 |
| 4,961,928 | 10/1990 | Holme et al. | 424/533 |
| 4,978,688 | 12/1990 | Louderback | 514/722 |
| 4,986,628 | 1/1991 | Lozhenko et al. | 385/31 |
| 4,992,363 | 2/1991 | Murphy | 435/2 |
| 4,994,367 | 2/1991 | Bode et al. | 435/2 |
| 4,998,931 | 3/1991 | Slichter et al. | 604/20 |
| 4,999,375 | 3/1991 | Bachynsky et al. | 514/455 |
| 5,011,695 | 4/1991 | Dichtelmuller et al. | 424/529 |
| 5,017,338 | 5/1991 | Surgenor | 422/41 |
| 5,020,995 | 6/1991 | Levy | 433/215 |
| 5,030,200 | 7/1991 | Judy et al. | 604/5 |
| 5,039,483 | 8/1991 | Sieber et al. | 422/28 |
| 5,041,078 | 8/1991 | Matthews et al. | 604/4 |
| 5,089,146 | 2/1992 | Carmen et al. | 210/782 |
| 5,089,384 | 2/1992 | Hale | 435/173.4 |
| 5,092,773 | 3/1992 | Levy | 433/224 |
| 5,114,670 | 5/1992 | Duffey | 422/24 |
| 5,114,957 | 5/1992 | Hendler et al. | 514/356 |
| 5,120,649 | 6/1992 | Horowitz et al. | 435/173.3 |
| 5,123,902 | 6/1992 | Müller et al. | 604/21 |
| 5,133,932 | 7/1992 | Gunn et al. | 422/24 |
| 5,147,776 | 9/1992 | Koerner, Jr. | 435/2 |
| 5,150,705 | 9/1992 | Stinson | 607/94 |
| 5,166,528 | 11/1992 | Le Vay | 250/455.11 |
| 5,184,020 | 2/1993 | Hearst et al. | 250/455.11 |
| 5,185,532 | 2/1993 | Zabsky et al. | 250/455.11 |
| 5,192,264 | 3/1993 | Fossel | 604/4 |
| 5,216,251 | 6/1993 | Matschke | 250/455.11 |
| 5,229,081 | 7/1993 | Suda | 427/186 |
| 5,232,844 | 8/1993 | Horowitz et al. | 435/173.1 |
| 5,234,808 | 8/1993 | Murphy | 435/2 |
| 5,236,716 | 8/1993 | Carmen et al. | 424/532 |
| 5,247,178 | 9/1993 | Ury et al. | 250/438 |
| 5,248,506 | 9/1993 | Holme et al. | 424/533 |
| 5,258,124 | 11/1993 | Bolton et al. | 210/748 |
| 5,269,946 | 12/1993 | Goldhaber et al. | 210/767 |
| 5,273,713 | 12/1993 | Levy | 422/22 |
| 5,288,605 | 2/1994 | Lin et al. | 435/2 |
| 5,288,647 | 2/1994 | Zimlich, Jr. et al. | 436/174 |
| 5,290,221 | 3/1994 | Wolf, Jr. et al. | 604/4 |
| 5,300,019 | 4/1994 | Bischof et al. | 604/4 |
| 5,304,113 | 4/1994 | Sieber et al. | 604/4 |
| 5,318,023 | 6/1994 | Vari et al. | 128/633 |
| 5,340,716 | 8/1994 | Ullman et al. | 435/6 |
| 5,342,752 | 8/1994 | Platz et al. | 435/2 |
| 5,344,752 | 9/1994 | Murphy | 435/2 |
| 5,344,918 | 9/1994 | Dazey et al. | 530/381 |
| 5,358,844 | 10/1994 | Stossel et al. | 435/2 |
| 5,360,734 | 11/1994 | Chapman et al. | 435/238 |
| 5,366,440 | 11/1994 | Fossel | 604/4 |
| 5,376,524 | 12/1994 | Murphy et al. | 435/2 |
| 5,378,601 | 1/1995 | Gepner-Puszkin | 435/2 |
| 5,418,130 | 5/1995 | Platz et al. | 435/2 |
| 5,419,759 | 5/1995 | Naficy | 604/5 |
| 5,427,695 | 6/1995 | Brown | 210/805 |
| 5,433,738 | 7/1995 | Stinson | 607/92 |
| 5,459,030 | 10/1995 | Lin et al. | 435/2 |
| 5,466,573 | 11/1995 | Murphy et al. | 435/2 |
| 5,474,891 | 12/1995 | Murphy | 435/2 |
| 5,482,828 | 1/1996 | Lin et al. | 435/2 |
| 5,487,971 | 1/1996 | Holme et al. | 435/2 |
| 5,503,721 | 4/1996 | Hearst et al. | 204/157.6 |
| 5,516,629 | 5/1996 | Park et al. | 435/2 |
| 5,527,704 | 6/1996 | Wolf, Jr. et al. | 435/283.1 |
| 5,536,238 | 7/1996 | Bischof | 604/6 |
| 5,545,516 | 8/1996 | Wagner | 435/2 |
| 5,547,635 | 8/1996 | Duthie, Jr. | 422/4 |
| 5,550,111 | 8/1996 | Suhadolnik et al. | 514/44 |
| 5,556,958 | 9/1996 | Carroll et al. | 536/25.3 |
| 5,556,993 | 9/1996 | Wollowitz et al. | 549/282 |
| 5,557,098 | 9/1996 | D'Silva | 250/222.1 |
| 5,569,579 | 10/1996 | Murphy | 435/2 |
| 5,571,666 | 11/1996 | Floyd et al. | 435/2 |
| 5,587,490 | 12/1996 | Goodrich, Jr. et al. | 549/282 |
| 5,593,823 | 1/1997 | Wollowitz et al. | 435/2 |
| 5,597,722 | 1/1997 | Chapman et al. | 435/238 |
| 5,607,924 | 3/1997 | Magda et al. | 514/44 |
| 5,622,867 | 4/1997 | Livesey et al. | 436/18 |
| 5,624,435 | 4/1997 | Furumoto et al. | 606/10 |
| 5,628,727 | 5/1997 | Hakky et al. | 604/6 |
| 5,639,376 | 6/1997 | Lee et al. | 210/645 |

| | | | |
|---|---|---|---|
| 5,639,382 | 6/1997 | Brown | 210/739 |
| 5,643,334 | 7/1997 | Eckhouse et al. | 607/88 |
| 5,652,096 | 7/1997 | Cimino | 435/6 |
| 5,653,887 | 8/1997 | Wahl et al. | 210/745 |
| 5,654,443 | 8/1997 | Wollowitz et al. | 549/282 |
| 5,658,530 | 8/1997 | Dunn | 422/24 |
| 5,658,722 | 8/1997 | Margolis-Nunno et al. | 435/2 |
| 5,683,661 | 11/1997 | Hearst et al. | 422/186.3 |
| 5,683,768 | 11/1997 | Shang et al. | 428/35.2 |
| 5,686,436 | 11/1997 | Van Dyke | 514/171 |
| 5,688,475 | 11/1997 | Duthie, Jr. | 422/186.3 |
| 5,691,132 | 11/1997 | Wollowitz et al. | 435/2 |
| 5,698,524 | 12/1997 | Mach et al. | 514/22 |
| 5,698,677 | 12/1997 | Eibl et al. | 530/381 |
| 5,702,684 | 12/1997 | McCoy et al. | 424/10.3 |
| 5,707,401 | 1/1998 | Talmore | 607/88 |
| 5,709,653 | 1/1998 | Leone | 604/20 |
| 5,709,991 | 1/1998 | Lin et al. | 435/2 |
| 5,712,086 | 1/1998 | Horowitz et al. | 435/2 |
| 5,714,328 | 2/1998 | Magda et al. | 435/6 |
| 5,739,013 | 4/1998 | Budowsky et al. | 435/91.1 |
| 5,756,553 | 5/1998 | Iguchi et al. | 514/772.3 |
| 5,772,960 | 6/1998 | Ito et al. | 422/41 |
| 5,789,150 | 8/1998 | Margolis-Nunno et al. | 435/2 |
| 5,789,601 | 8/1998 | Park et al. | 549/283 |
| 5,798,238 | 8/1998 | Goodrich, Jr. et al. | 435/173.3 |
| 5,798,523 | 8/1998 | Villenueve et al. | 250/234 |
| 5,827,644 | 10/1998 | Floyd et al. | 435/2 |
| 5,834,198 | 11/1998 | Famulok et al. | 435/6 |
| 5,843,459 | 12/1998 | Wang et al. | 424/231.1 |
| 5,846,961 | 12/1998 | Van Dyke | 514/171 |
| 5,854,967 | 12/1998 | Hearst et al. | 422/186.3 |
| 5,869,701 | 2/1999 | Park et al. | 549/283 |
| 5,871,900 | 2/1999 | Wollowitz et al. | 435/2 |
| 5,922,278 | 7/1999 | Chapman et al. | 422/22 |
| 6,020,333 | 2/2000 | Berque | 514/251 |

OTHER PUBLICATIONS

Ennever, J.F. and Speck, W.T., "Short Communication. Photochemical Reactions of Riboflavin: Covalent Binding to DNA and to Poly (Da)•Poly (Dt)," (1983) *Pediatr. Res.* 17:234–236.

Product advertisement for "Ultracure 100SS Plus Specifications," EFOS USA, Inc., Williamsville, NY, USA.

Brodie, A.F. and Watanabe, T., "Mode of action of vitamin K in microorganisms," (1966) *Vitam. Horm.* 24:447–463.

Chow, C.S. and Barton, J.K., "Recognition of G–U mismatches by tris(4,7-diphenyl-1,10-phenanthroline)rhodium(III)," (1992) *Biochemistry* 31(24):5423–5429.

Deutsch, E., "Vitamin K in medical practice: adults," (1966) *Vitam. Horm.* 24:665–680.

Joshi, P.C., "Comparison of the DNA–damaging property of photosensitized riboflavin via singlet oxygen ($^1O_2$) and superoxide radical ($O_i^-$) mechanisms," (1985) *Toxicology Letters* 26:211–217.

Klebanoff, M.A. et al., "The risk of childhood cancer after neonatal exposure to vitamin K," (1993) *New Eng.. J. Med.* 329(13):905–908.

Leontis, N.B. and Westhof, E., "The 5S rRNA loop E: chemical probing and phylogenetic data versus crystal structure," (1998) *RNA* 4:1134–1153.

Lim, A.C. and Barton, J.K., "Chemical probing of tDNA$^{Phe}$ with transition metal complexes: a structural comparison of RNA and DNA," (1993) *Biochemistry* 32:11029–11034.

Maddox, J., "The working of vitamin K," (1991) *Nature* 353(6346):695.

McCord, E.F., "Chemically induced dynamic nuclear polarization studies of yeast," (1984) *Biochemistry* 23:1935–1939.

Merenstein, G.B. et al. (Vitamin K Ad Hoc Task Force), "Controversies concerning vitamin K and the newborn," (1993) *Pediatrics* 91(5):1001–1003.

Merrifield, L.S. and Yang, H.Y., "Factors affecting the antimicrobial activity of vitamin K5," (1965) *Appl. Microbiol.* 13(5):766–770.

Merrifield, L.S. and Yang, H.Y., "Vitamin K5 as a fungistatic agent," (1965) *Applied Microbiol.* 13(5):660–662.

Murata, A. et al., "Effect of vitamins other than vitamin C on viruses: virus–inactivating activity of vitamin K5," (1983) *J. Nutr. Sci. Vitaminol (Tokyo)* 29(6):721–724.

Naseem, I. et al., "Effect of alkylated and intercalated DNA on the generation of superoxide anion by riboflavin," (1988) *Bioscience Reports* 8(5):485–492.

Pratt, R. et al., "Vitamin $K_5$ as an Antimicrobial Medicament and Preservative," (1950) *J. Am. Pharm. Ass'n* 39(3):127–134.

Shwartzman, G., "Antibacterial Properties of 4–Amino–2–Methyl–1–Naphthol Hydrochloride," (1948)*Proc. Soc. Exp. Biol. Med.* 67:376–378.

Spranger, J., "Does vitamin K cause cancer?" (1993) *Eur. J. Pediatr.* 152(2):174.

Vest, M., "Vitamin K in medical practice: pediatrics," (1966) *Vitam. Horm.* 24:649–663.

Yang, H.Y. et al., "Vitamin $K_5$ as a Food Preservative," (1958) *Food Technology* 501–504.

Kabuta, H. et al., "Inactivation of viruses by dyes and visible light," (1978) *Chemical Abstracts* 87(1), Abstract No. 400626.

Kale, H. et al., "Assessment of the genotoxic potential of riboflavin and lumiflavin; B. Effect of light," (1992) *Mutation Research* 298:17–23.

Kobayashi et al., "The molecular mechanism of mutation. Photodynamic action of flavins on the RNA–synthesizing system," (1983) *Chemical Abstracts* 98(1) Abstract No. 1200.

North et al., "Photosensitzers as Virucidal Agents", J. Photochem. Photobiol., 17(2), pp. 99–108, Feb. 1993.*

Hansen C. V., "Photochemical and Ribonucleic Inactivation of Deoxyribonucleic Acid Viruses by Chlorpromazine", Antimicrob. Agent Chemother., 15(3), pp. 461–464, Mar. 1979.*

Malik et al., "New Trends in Photobiology—Bactericidal Effects of Photoactivated Porhyrins—An Altenative Approach to Antimicrobial Drugs", J. Photochem. Photobiol. Pt.B:Biology, vol. 5, pp. 281–293, 1990.*

Abdurashidova, G.G. et al., "Polynucleotide–protein itneractions in the translation system. Identification of proteins itneracting with tRNA in the A–and P–sites of E. coli ribosomes," (1979) *Nucleic Acids Res.* 6(12):3891–3909.

Budowsky, E.I. et al., "Induction of polynucleotide–protein cross–linkages by ultraviolet irradiation," (1986) *Eur. J. Biochem.* 159:95–101.

Budowsky, E.I. and Abdurashidova, G.G., "Polynucleotide–Protein Cross–Links Induced by Ultraviolet Light and Their Use for Structural Investigation of Nucleoproteins," (1989) *Progress in Nucleic Acid Res. and Mol. Biol.* 37:1–65.

Budowsky, E.I., "Problems and Prospects for Preparation of Killed Antiviral Vaccines," (1991) *Adv. Virus Res.* 39:255–290.

Budowsky, E.I. et al., "Principles of selective inactivation of viral genome. VI. Inactivation of the infectivity of the influenza virus by the action of β–propiolactone," (1991) *Vaccine* 9:398–402.

Budowsky, E.I. et al., "Principles of selective inactivation of viral genome. VII. Some peculiarities in determination of viral suspension infectivity during inactivation by chemical agents," (1991) *Vaccine* 9:473–476.

Budowsky, E.I. et al., "Principles of selective inactivation of viral genome. VIII. The influence of β–propiolactone on immunogenic and protective activities of influenza virus," (1993) *Vaccine* 11(3):343–348.

Budowsky, E.I. et al., "Preparaion of cyclic 2',3'–monophosphates of oligoadenylates (A2'p)$_n$A>p and A3'p(A2'p)$_{n-1}$A>p," (1994) *Eur. J. Biochem.* 220:97–104.

Cadet, J. et al., "Mechanisms and Products of Photosensitized Degradation of Nucleic Acids and Related Model Compounds," (1983) *Israel J. Chem.* 23:420–429.

Goodrich, R.P. and Platz, M.S., "The design and development of selective, photoactivated drugs for sterilization of blood products," (1997) *Drugs of the Future* 22(2):159–171.

Hoffman, M.E. and Meneghini, R., "DNA Strand Breaks in Mammalian Cells Exposed to Light in the Presence of Riboflavin and Tryptophan," (1979) *Photochemistry and Photobiology* 29:299–303.

Ivanchenko, V.A. et al., "The photochemistry of purine components of nucleic acids. I. The efficiency of photolysis of adenine and guanine derivatives in aqueous solution," (1975) *Nucleic Acids Res.* 2(8):1365–1373.

Korycka–Dahl, M. and Richardson, T., "Photodegradation of DNA with Fluorescent Light in the Presence of Riboflavin, and Photoprotection by Flavin Triplet–State Quenchers," (1980) *Biochemica et Biophysica Acta* 610:229–234.

Kovalsky, O.I. and Budowsky, E.I., "Laser (Two–Quantum) Photolysis of Polynucleotides and Nucleoproteins: Quantitative Processing of Results," 1990, *Photochemistry and Photobiology* 5(6):659–665.

Kuratomi, K. and Kobayashi, Y., "Studies on the Interactions Between DNA and Flavins," (1977) *Biochemica et Biophysica Acta* 476:207–217.

Peak, J.G. et al., "DNA Breakage Caused by 334–nm Ultraviolet Light is Enhanced by Naturally Occurring Nucleic Acid Components and Nucleotide Coenzymes," (1984) *Photochemistry and Photobiology* 39:(5)713–716.

Piette, J. et al., "Alteration of Guanine Residues During Proflaving Mediated Photosensitization of DNA," (1981) *Photochemistry and Photobiology* 33:325–333.

Piette, J. et al., "Production of Breaks in Single–and Double–Stranded Forms of Bacteriophage φX174 DNA by Proflavine and Light Treatment," (1979) *Photochemistry and Photobiology* 30:369–378.

Simukova, N.A. and Budowsky, E.I., "Conversion of Non–Covalent Interactions in Nucleoproteins in to Covalent Bonds: UV–Induced Formation of Polynucleotide–Protein Crosslinks in Bacteriophage Sd Virions," (1974) *FEBS Letters* 38(3):299–303.

Speck, W.T. et al., "Further Observations on the Photooxidation of DNA in the Presence of Riboflavin," (1976) *Biochimica et Biphysica Acta* 435:39–44.

Tsugita, A. et al., "Photosensitized inactivation of ribonucleic acids in the presence of riboflavin," (1965) *Biochim. Biophys. Acta* 103:360–363.

Webb, R.B. and Malina, M.M., "Mutagenesis in Escherichia coli by Visible Light," (1967) *Science* 156:1104–1105.

\* cited by examiner

—— 3.2 mm acrylic
- - - - 3.2 mm UV acrylic
— — 3.2 mm PS
⋯+⋯+⋯ 3.2 mm PC

METHOD AND APPARATUS FOR INACTIVATION OF BIOLOGICAL CONTAMINANTS USING ENDOGENOUS ALLOXAZINE OR ISOALLOXAZINE PHOTOSENSITIZERS

BACKGROUND

Contamination of blood supplies with infectious microorganisms such as HIV, hepatitis and other viruses and bacteria presents a serious health hazard for those who must receive transfusions of whole blood or administration of various blood components such as platelets, red cells, blood plasma, Factor VIII, plasminogen, fibronectin, antithrombin III, cryoprecipitate, human plasma protein fraction, albumin, immune serum globulin, prothrombin complex plasma growth hormones, and other components isolated from blood. Blood screening procedures may miss contaminants, and sterilization procedures which do not damage cellular blood components but effectively inactivate all infectious viruses and other microorganisms have not heretofore been available.

Solvent detergent methods of blood component sterilization work by dissolving phospholipid membranes surrounding viruses such as HIV, and do not damage protein components of blood; however, if blood cells are present, such methods cannot be used because of damage to cell membranes.

The use of photosensitizers, compounds which absorb light of a defined wavelength and transfer the absorbed energy to an energy acceptor, has been proposed for blood component sterilization. For example, European Patent application 196,515 published Oct. 8, 1986, suggests the use of non-endogenous photosensitizers such as porphyrins, psoralens, acridine, toluidines, flavine (acriflavine hydrochloride), phenothiazine derivatives, and dyes such as neutral red, and methylene blue, as blood additives. Protoporphyrin, which occurs naturally within the body, is exemplified as one such photosensitizer; however, its usefulness is limited in that it cannot be used in the presence of the common blood component albumin. Chlorpromazine, is also exemplified as one such photosensitizer; however its usefulness is limited by the fact that it should be removed from any fluid administered to a patient after the decontamination procedure because it has a sedative effect.

Goodrich, R. P., et al. (1997), "The Design and Development of Selective, Photoactivated Drugs for Sterilization of Blood Products," Drugs of the Future 22:159–171 provides a review of some photosensitizers including psoralens, and some of the issues of importance in choosing photosensitizers for decontamination of blood products. The use of texaphyrins for DNA photocleavage is described in U.S. Pat. Nos. 5,607,924 issued Mar. 4, 1997 and 5,714,328 issued Feb. 3, 1998 to Magda et al. The use of sapphyrins for viral deactivation is described in U.S. Pat. No. 5,041,078 issued Aug. 20, 1991 to Matthews, et al. Inactivation of extracellular enveloped viruses in blood and blood components by Phenthiazin-5-ium dyes plus light is described in U.S. Pat. No. 5,545,516 issued Aug. 13, 1996 to Wagner. The use of porphyrins, hematoporphyrins, and merocyanine dyes as photosensitizing agents for eradicating infectious contaminants such as viruses and protozoa from body tissues such as body fluids is disclosed in U.S. Pat. No. 4,915,683 issued Apr. 10, 1990 and related U.S. Pat. No. 5,304,113 issued Apr. 19, 1994 to Sieber et al. The mechanism of action of such photosensitizers is described as involving preferential binding to domains in lipid bilayers, e.g. on enveloped viruses and some virus-infected cells. Photoexcitation of membrane-bound agent molecules leads to the formation of reactive oxygen species such as singlet oxygen which causes lipid peroxidation. A problem with the use of such photosensitizers is that they attack cell membranes of desirable components of fluids to be decontaminated, such as red blood cells, and the singlet oxygen also attacks desired protein components of fluids being treated. U.S. Pat. No. 4,727,027 issued Feb. 23, 1988 to Wiesehahn, G. P., et al. discloses the use of furocoumarins including psoralen and derivatives for decontamination of blood and blood products, but teaches that steps must be taken to reduce the availability of dissolved oxygen and other reactive species in order to inhibit denaturation of biologically active proteins. Photoinactivation of viral and bacterial blood contaminants using halogenated coumarins is described in U.S. Pat. No. 5,516,629 issued May 14, 1996 to Park, et al. U.S. Pat. No. 5,587,490 issued Dec. 24, 1996 to Goodrich Jr., R. P., et al. and U.S. Pat. No. 5,418,130 to Platz, et al. disclose the use of substituted psoralens for inactivation of viral and bacterial blood contaminants. The latter patent also teaches the necessity of controlling free radical damage to other blood components. U.S. Pat. No. 5,654,443 issued Aug. 5, 1997 to Wollowitz et al. teaches new psoralen compositions used for photodecontamination of blood. U.S. Pat. No. 5,709,991 issued Jan. 20, 1998 to Lin et al. teaches the use of psoralen for photodecontamination of platelet preparations and removal of psoralen afterward. U.S. Pat. No. 5,120,649 issued Jun. 9, 1992 and related U.S. Pat. No. 5,232,844 issued Aug. 3, 1993 to Horowitz, et al., also disclose the need for the use of "quenchers" in combination with photosensitizers which attack lipid membranes, and U.S. Pat. No. 5,360,734 issued Nov. 1, 1994 to Chapman et al. also addresses this problem of prevention of damage to other blood components.

Photosensitizers which attack nucleic acids are known to the art. U.S. Pat. No. 5,342,752 issued Aug. 30, 1994 to Platz et al. discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. This patent fails to disclose an apparatus for decontaminating blood on a flow-through basis.

Binding of DNA with photoactive agents has been exploited in processes to reduce lymphocytic populations in blood as taught in U.S. Pat. No. 4,612,007 issued Sep. 16, 1986 and related U.S. Pat. No. 4,683,889 issued Aug. 4, 1987 to Edelson.

Riboflavin 7,8-dimethyl-10-ribityl isoalloxazine has been reported to attack nucleic acids. Photoalteration of nucleic acid in the presence of 7,8-dimethyl-10-ribityl isoalloxazine is discussed in Tsugita, A, et al. (1965), "Photosensitized inactivation of ribonucleic acids in the presence of riboflavin," Biochimica et Biophysica Acta 103:360–363; and Speck, W. T. et al. (1976), "Further Observations on the Photooxidation of DNA in the Presence of Riboflavin," Biochimica et Biophysica Acta 435:39–44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207–217. Hoffinann, M. E., et al. (1979), "DNA Strand Breaks in Mammalian Cells Exposed to Light in the Presence of Riboflavin and Tryptophan," Photochemistry and Photobiology 29:299–303 describes the use of 7,8-dimethyl-10-ribityl isoalloxazine and tryptophan to induce breaks in DNA of mammalian cells after exposure to visible fluorescent light or near-ultraviolet light. The article states that these effects did not occur if either 7,8-dimethyl-10-ribityl isoalloxazine or tryptophan was omitted from the medium. DNA strand breaks upon exposure to proflavine and light are reported in Piette, J. et al. (1979), "Production of Breaks in Single- and Double-stranded Forms of Bacteriophage ΦX174 DNA by Proflavine and Light Treatment," Photochemistry and Photobiology 30:369–378, and alteration of guanine residues during proflavine -mediated photosensitization of DNA is discussed in Piette, J., et al. (1981), "Alteration of Guanine Residues during Proflavine Mediated Photosensitization of DNA," Photochemistry and Photobiology 33:325–333.

J. Cadet, et al. (1983), "Mechanisms and Products of Photosensitized Degradation of Nucleic Acids and Related Model Compounds," Israel J. Chem. 23:420–429, discusses the mechanism of action by production of singlet oxygen of rose bengal, methylene blue, thionine and other dyes, compared with mechanisms not involving production of singlet oxygen by which nucleic acid attack by flavin or pteron derivatives proceeds. 7,8-dimethyl-10-ribityl isoalloxazine is exemplified in this disclosure as having the ability to degrade nucleic acids. Korycka-Dahl, M., et al. (1980), "Photodegradation of DNA with Fluorescent Light in the Presence of Riboflavin, and Photoprotection by Flavin Triplet-State Quenchers," Biochimica et Biophysica Acta 610:229–234 also discloses that active oxygen species are not directly involved in DNA scission by riboflavin. Peak, J. G., et al. (1984), "DNA Breakage Caused by 334-mn Ultraviolet Light is Enhanced by Naturally Occurring Nucleic Acid Components and Nucleotide Coenzymes," Photochemistry and Photobiology 39:713–716 further explores the mechanism of action of riboflavin and other photosensitizers. However, no suggestion is made that such photosensitizers be used for decontamination of medical fluids.

Apparatuses for decontamination of blood have been described in U.S. Pat. No. 5,290,221 issued Mar. 1, 1994 to Wolfe, Jr., et al. and U.S. Pat. No. 5,536,238 issued Jul. 16, 1996 to Bischof. U.S. Pat. No. 5,290,221 discloses the irradiation of fluid in a relatively narrow, arcuate gap. U.S. Pat. No. 5,536,238 discloses devices utilizing optical fibers extending into a filtration medium. Both patents recommend as photosensitizers benzoporphryin derivatives which have an affinity for cell walls.

All publications referred to herein are hereby incorporated by reference to the extent not inconsistent herewith.

SUMMARY

Methods and apparatuses are provided for inactivation of microorganisms in materials such as fluids which also contain one or more components selected from the group consisting of biologically active protein, blood and blood constituents, without destroying the biological activity of such components. The methods comprise:

(a) mixing an effective, non-toxic amount of an endogenous photosensitizer with the fluid;

(b) exposing the fluid to photoradiation sufficient to activate the endogenous photosensitizer; and (c) allowing the activated endogenous photosensitizer to interfere with nucleic acid present in microorganisms in the fluid so that the microorganisms are inactivated.

As used herein, the term "interfere with nucleic acid" with respect to a photosensitizer means the photosensitizer is positioned with respect to the nucleic acid, e.g., by binding, so as to prevent replication of the nucleic acid.

As used herein, the term "inactivation of a microorganism" means preventing the microorganism from replicating, either by killing the microorganism or otherwise interfering with its ability to reproduce.

Microorganisms include viruses, bacteria, fungi, and protozoa, preferably viruses. Exemplary viruses include acquired immunodeficiency (HIV) virus, hepatitis A, B and C viruses, human T-lymphotropic retroviruses, HTLV-III, lymphadenopathy virus LAV/IDAV, parvovirus and others known to the art.

Materials which may be treated by the methods of this invention include any materials which are adequately permeable to photoradiation to provide sufficient light to achieve viral inactivation, or which can be suspended or dissolved in fluids which have such permeability to photoradiation. Examples of such materials are aqueous compositions containing biologically active proteins derived from blood or blood constituents. Whole blood, packed red cells, platelets and plasma (fresh or fresh frozen plasma) are exemplary of such blood constituents. In addition, therapeutic protein compositions containing proteins derived from blood, such as fluids containing biologically active protein useful in the treatment of medical disorders, e.g. factor VIII, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen streptokinase complex, ceruloplasmin, transferrin, haptoglobin, antitrypsin and prekallikrein may be treated by the decontamination methods of this invention. The term "biologically active" means capable of effecting a change in a living organism or component thereof. The term "blood product" as used herein includes blood constituents and therapeutic protein compositions containing proteins derived from blood as defined above. Fluids containing biologically active proteins other than those derived from blood may also be treated by the methods of this invention.

Decontamination methods of this invention using endogenous photosensitizers do not destroy the biological activity of fluid components other than microorganisms. As much biological activity of these components as possible is retained, although in certain instances, when the methods are optimized, some loss of biological activity, e.g., denaturization of protein components, must be balanced against effective decontamination of the fluid.

The photosensitizers useful in this invention include any photosensitizers known to the art to be useful for inactivating microorganisms. A "photosensitizer" is defined as any compound which absorbs radiation of one or more defined wavelengths and subsequently transfers the absorbed energy to an energy acceptor. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers preferred in this invention include compounds which preferentially adsorb to nucleic acids, thus focusing their photodynamic effect upon microorganisms and viruses with little or no effect upon accompanying cells or proteins. Most preferred are endogenous photosensitizers. The term "endogenous" means naturally found in a human or mammalian body, either as a result of synthesis by the body or because of ingestion in common foodstuffs (e.g. vitamins) or formation of metabolites and byproducts in vivo. Examples of such endogenous photosensitizers are alloxazines such as 7,8-dimethyl-10-ribityl isoalloxazine, 7,8,10- trimethylisoalloxazine, and 7,8-dimethylalloxazine, vitamin Ks, vitamin L, and napththoquinones, naphthalenes, naphthols and their derivatives having planar molecular conformations. When endogenous photosensitizers are used, particularly when such photosensitizers are not inherently toxic or do not yield toxic photoproducts after photoradiation, no removal or purification step is required after decontamination, and treated product can be directly returned to a patient's body or administered to a patient in need of its therapeutic effect. Preferred endogenous photosensitizers are:

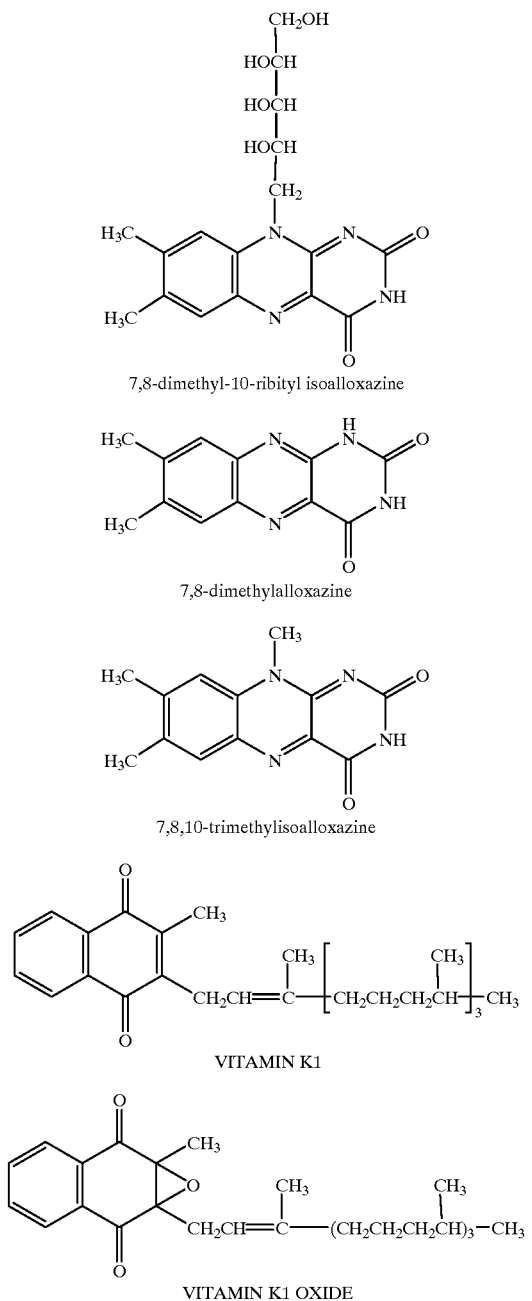

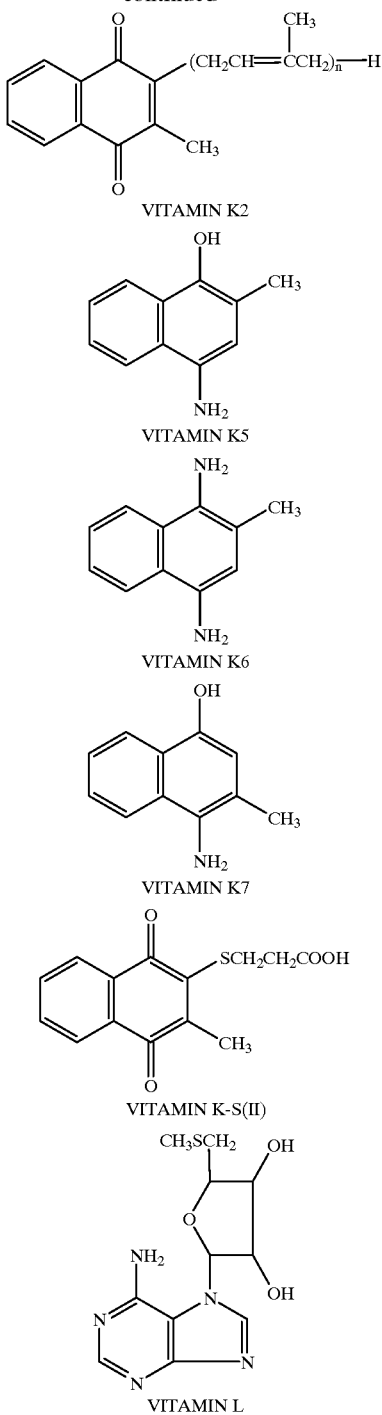

The method of this invention requires mixing the photosensitizer with the material to be decontaminated. Mixing may be done by simply adding the photosensitizer or a solution containing the photosensitizer to a fluid to be decontaminated. In a preferred embodiment, the material to be decontaminated to which photosensitizer has been added is flowed past a photoradiation source, and the flow of the material generally provides sufficient turbulence to distribute the photosensitizer throughout the fluid to be decontaminated.

The amount of photosensitizer to be mixed with the fluid will be an amount sufficient to adequately inactivate all microorganisms therein, but less than a toxic or insoluble amount. As taught herein, optimal concentrations for desired photosensitizers may be readily determined by those skilled in the art without undue experimentation. Preferably the photosensitizer is used in a concentration of at least about 1 $\mu$M. For 7,8-dimethyl-10-ribityl isoalloxazine a concentration range between about 1 $\mu$M and about 160 $\mu$M is preferred.

The fluid containing the photosensitizer is then exposed to photoradiation of the appropriate wavelength to activate the photosensitizer, using an amount of photoradiation sufficient to activate the photosensitizer as described above, but less than that which would cause non-specific damage to the biological components or substantially interfere with biological activity of other proteins present in the fluid. The wavelength used will depend on the photosensitizer selected, as is known to the art or readily determinable without undue experimentation following the teachings hereof. Preferably the light source is a fluorescent or luminescent source providing light of about 300 nm to about 700 nm, and more preferably about 340 nm to about 650 nm of radiation. Wavelengths in the ultraviolet to visible range are useful in this invention.

The activated photosensitizer is capable of inactivating the microorganisms present, preferably by interfering with, e.g. binding to, nucleic acid in the microorganisms to prevent their replication. "Nucleic acid" includes ribonucleic acid (RNA) and deoxyribonucleic acid (DNA). Some photosensitizers may act by binding to cell membranes or by other mechanisms; however, nucleic-acid-targeted photosensitizers (i.e. those which bind to nucleic acid) are preferred.

The fluid containing the photosensitizer is preferably flowed into a photopermeable container for irradiation. The term "container" may refer to a closed or open space, which may be made of rigid or flexible material, e.g., may be a bag or box or trough. It may be closed or open at the top and may have openings at both ends, e.g., may be a tube, to allow for flow-through of fluid therein. A cuvette has been used to exemplify the invention. The term "photopermeable" means the material of the container is adequately transparent to photoradiation of the proper wavelength for activating the photosensitizer, and has a depth (dimension measured in the direction of the radiation from the photoradiation source) sufficient to allow photoradiation to adequately penetrate the container to contact photosensitizer molecules at all distances from the light source and ensure inactivation of microorganisms in the fluid to be decontaminated, and a length (dimension in the direction of fluid flow) sufficient to ensure a sufficient exposure time of the fluid to the photoradiation. The materials for making the containers, depths and lengths of containers may be easily determined by those skilled in the art without undue experimentation following the teachings hereof, and together with the flow rate of fluid through the container, the intensity of the photoradiation and the absorptivities of the fluid components, e.g., plasma, platelets, red blood cells, will determine the amount of time the fluid needs to be exposed to photoradiation. For 7,8-dimethyl-10-ribityl isoalloxazine, a preferred amount of radiation is between about 1 J/cm$^2$ to 30 J/cm$^2$.

In a preferred embodiment, the light source is connected to the photopermeable container for the fluid by means of a light guide such as a light channel or fiber optic tube which prevents scattering of the light between the source and the container for the fluid, and more importantly, prevents substantial heating of the fluid within the container. Direct exposure to the light source may raise temperatures as much as 10 to 15° C., which can cause denaturization of blood components. Use of the light guide keeps any heating to less than about 2° C. The method may also include the use of temperature sensors and cooling mechanisms where necessary to keep the temperature below temperatures at which desired proteins in the fluid are damaged. Preferably, the temperature is kept between about 0° C. and about 45° C., more preferably between about 4° C. and about 37° C., and most preferably about 22° C.

This invention also provides a system for inactivation of microorganisms in a fluid containing such microorganisms comprising:
(a) means for adding an effective, non-toxic amount of a photosensitizer to the fluid;
(b) a photopermeable container for the fluid in fluid communication with the means for adding photosensitizer having a depth and length selected to allow exposure of the fluid therein to an amount of photoradiation sufficient to activate the photosensitizer at a selected flow rate;
(c) means for producing the selected flow rate of fluid through the container, and
(d) a photoradiation source for providing sufficient photoradiation to the fluid in the photopermeable container of a type and amount selected to activate the photosensitizer.

Any means for adding the photosensitizer to the fluid to be decontaminated known to the art may be used, such means typically including flow conduits, ports, reservoirs, valves, and the like. Preferably, the system includes means such as pumps or adjustable valves for controlling the flow of the photosensitizer into the fluid to be decontaminated so that its concentration may be controlled between effective and toxic levels as described above. In a preferred embodiment, photosensitizer is mixed with the anticoagulant feed to a blood apheresis system. For endogenous photosensitizers having sugar moieties, the pH of the solution is preferably kept low enough, as is known to the art, to prevent detachment of the sugar moiety.

The photopermeable container is preferably a transparent cuvette made of polycarbonate, glass, quartz, polystyrene, polyvinyl chloride, polyolefin, or other transparent material. The cuvette may be enclosed in a radiation chamber having mirrored walls. A photoradiation enhancer such as a second photoradiation source or reflective surface may be placed adjacent to the cuvette to increase the amount of photoradiation contacting the fluid within the cuvette. The system preferably includes a pump for adjusting the flow rate of the fluid to desired levels to ensure substantial decontamination as described above. The cuvette has a length, coordinated with the flow rate therethrough, sufficient to expose fluid therein to sufficient photoradiation to effect substantial decontamination thereof.

Also preferably the cuvette is spaced apart from the light source a sufficient distance that heating of the fluid in the cuvette does not occur, and light is transmitted from the light source to the cuvette by means of a light guide.

Such decontamination systems may be designed as stand-alone units or may be easily incorporated into existing apparatuses known to the art for separating or treating blood being withdrawn from or administered to a patient. For example, such blood-handling apparatuses include the COBE Spectra™ or TRIMA® apheresis systems, available from Cobe Laboratories, Inc., Lakewood, Co., or the apparatuses described in U.S. Pat. No. 5,653,887 and U.S. Ser. No. 08/924,519 filed Sep. 5, 1997 (PCT Publication WO 99/11305 dated Mar. 11, 1999 of Cobe Laboratories, Inc. The decontamination system may be inserted just downstream of the point where blood is withdrawn from a patient or donor, just prior to insertion of blood product into a patient, or at any point before or after separation of blood constituents. The photosensitizer is added to blood components along with anticoagulant in a preferred embodiment, and separate irradiation sources and cuvettes are placed immediately upstream from collection points for platelets, for plasma and for red blood cells. The use of three separate blood decontamination systems is preferred to placement of a single blood decontamination system upstream of the blood separation vessel of an apheresis system because the lower flow rates in the separate component lines allows greater ease of irradiation. In this way irradiation of white blood cells can be avoided as well. In other embodiments, decontamination systems of this invention may be used to process previously collected and stored blood products.

The endogenous photosensitizers disclosed herein can be used in pre-existing blood component decontamination systems as well as in the decontamination system disclosed herein. For example, the endogenous photosensitizers of this invention can be used in the decontamination systems described in U.S. Pat. Nos. 5,290,221, 5,536,238, 5,290,221 and 5,536,238.

DETAILED DESCRIPTION

The decontamination method of this invention using endogenous photosensitizers is exemplified herein using 7,8-dimethyl-10-ribityl isoalloxazine as the photosensitizer, however, any photosensitizer may be used which is capable of being activated by photoradiation to cause inactivation of microorganisms. The photosensitizer must be one which does not destroy desired components of the fluid being decontaminated, and also preferably which does not break down as a result of the photoradiation into products which significantly destroy desired components or have significant toxicity. The wavelength at which the photosensitizer is activated is determined as described herein, using literature sources or direct measurement. Its solubility in the fluid to be decontaminated or in a combination of carrier fluid and fluid to be contaminated is also determined. The ability of photoradiation at the activating wavelength to penetrate the fluid to be decontaminated must also be determined as taught herein. Appropriate temperatures for the reaction of the photosensitizer with its substrate are determined, as well as the ranges of temperature, photoradiation intensity and duration, and photosensitizer concentration which will optimize microbial inactivation and minimize damage to desired proteins in the fluid. Examples 1–7 and FIGS. 1–5 illustrate the determination of information required to develop a decontamination system of this invention.

Figure 6:
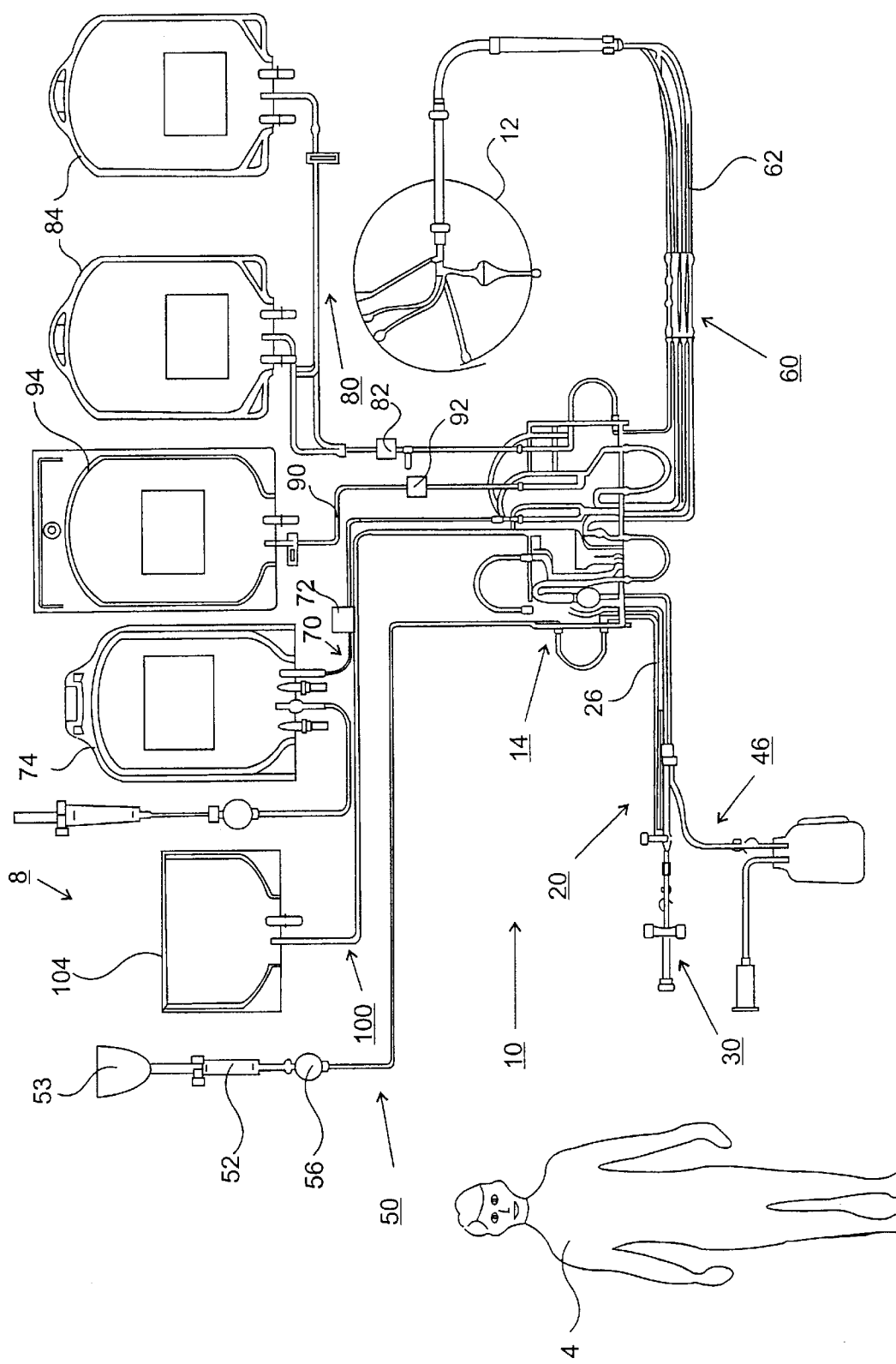
FIG. 6 depicts a blood separation apparatus incorporating the photoradiation device of this invention.
Figure 7:
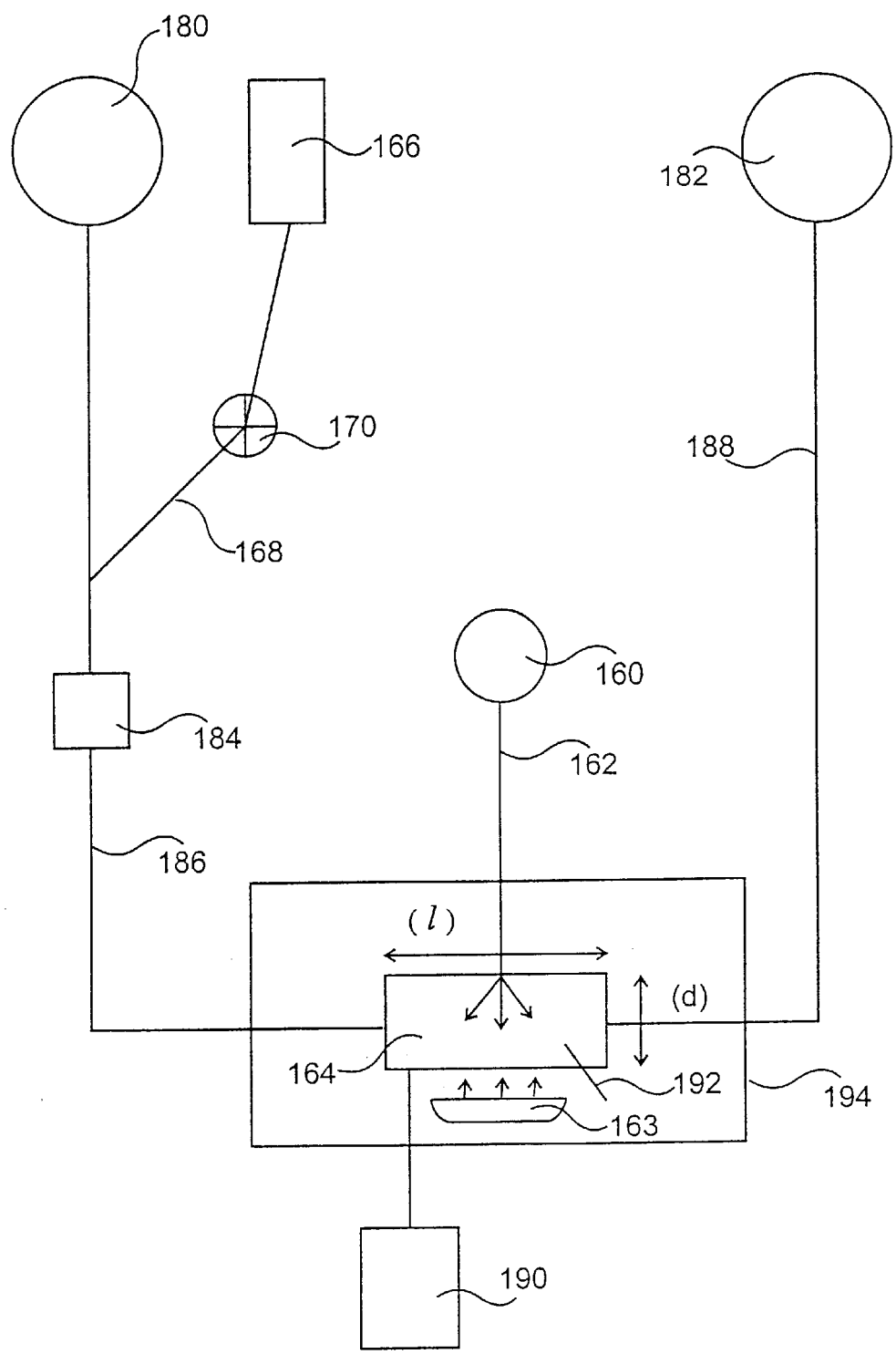
FIG. 7 depicts the decontamination assembly of this invention.

Once such system requirements have been determined, apparatuses may be designed which provide the correct flow rates, photoperneabilities, and light intensities to cause inactivation of microorganisms present in the fluid, as is taught herein. The fluid to be decontaminated is mixed with photosensitizer and then irradiated with a sufficient amount of photoradiation to activate the photosensitizer to react with microorganisms in the fluid such that microorganisms in the fluid are inactivated. The amount of photoradiation reaching microorganisms in the fluid is controlled by selecting an appropriate photoradiation source, an appropriate distance of the photoradiation source from the fluid to be decontaminated, which may be increased through the use of light guides to carry the photoradiation directly to the container for the fluid, an appropriate photopermeable material for the container for the fluid, an appropriate depth to allow full penetration of the photoradiation into the container, photoradiation enhancers such as one or more additional photoradiation sources, preferably on the opposite side of the container from the first, or reflectors to reflect light from the radiation source back into the container, appropriate flow rates for the fluid in the container and an appropriate container length to allow sufficient time for inactivation of microorganisms present. Temperature monitors and controllers may also be required to keep the fluid at optimal temperature. FIG. 6 depicts a decontamination system of this invention as part of an apparatus for separating blood components, and FIG. 7 provides details of a preferred decontamination system.

The method preferably uses endogenous photosensitizers, and more preferably endogenous photosensitizers which function by interfering with nucleic acid replication. 7,8-dimethyl-10-ribityl isoalloxazine is the preferred photosensitizer for use in this invention. The chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). Cadet et al. (1983) J. Chem., 23:420–429, clearly demonstrate the effects of 7,8-dimethyl-10-ribityl isoalloxazine are due to non-singlet oxygen oxidation of guanosine residues. In addition, adenosine bases appear to be sensitive to the effects of 7,8-dimethyl-10-ribityl isoalloxazine plus UV light. This is important since adenosine residues are relatively insensitive to singlet oxygen-dependent processes. 7,8-dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species. Since indiscriminate damage to cells and proteins arises primarily from singlet oxygen sources, this mechanistic pathway for the action of 7,8- dimethyl-10-ribityl isoalloxazine allows greater selectivity in its action than is the case with compounds such as psoralens which possess significant Type II chemistry.

FIG. 6 shows a blood apparatus device and apheresis system incorporating the photoradiation devices of this invention. Whole blood is withdrawn from a donor/patient 4 and is provided to an apheresis system or blood component separation device 8 where the blood is separated into the various component types and at least one of these blood component types is removed from the device 8. These blood components may then be provided for subsequent use by another or may undergo a therapeutic treatment and be returned to the donor/patient 4.

In the blood component separation device 8, blood is withdrawn from the donor/patient 4 and directed through an extracorporeal tubing circuit 10 and a blood-processing vessel 12, defining a completely closed and sterile system. The blood component separation device 8 is connected to a pump (not shown). Blood flows from the donor/patient 4 through the extracorporeal tubing circuit 10 and into rotating blood processing vessel 12. The blood within the blood processing vessel 12 is separated into various blood component types, and these component types (platelets, plasma, red blood cells) are continually removed from the blood processing vessel 12. Blood components which are not being retained for collection or for therapeutic treatment (e.g., red blood cells, white blood cells, plasma) are also removed from the blood processing vessel 12 and returned to the donor/patient 4 via the extracorporeal tubing circuit 10.

Operation of the blood component separation device is preferably controlled by one or more computer processors included therein.

Blood-primable extracorporeal tubing circuit 10 comprises a cassette assembly 14 and a number of tubing assemblies 20, 50, 60, 80, 90, 100 interconnected therewith. Blood removal/return tubing assembly 20 provides a single needle interface between a donor/patient 4 and cassette assembly 14, and blood inlet/blood component tubing subassembly 60 provides the interface between cassette assembly 14 and blood processing vessel 12. An anticoagulant tubing assembly 50, platelet collection tubing assembly 80, plasma collection tubing assembly 90, red blood cell collection tubing assembly 70 and vent bag tubing subassembly 100 are also interconnected with cassette assembly 14.

The blood removal/return tubing assembly 20 includes a needle subassembly 30 interconnected therewith and anticoagulant tubing 26 connecting to anticoagulant tubing assembly 50 through cassette assembly 14.

Cassette assembly 14 includes front and back molded plastic plates that are hot-welded together to define a rectangular cassette member having integral fluid passageways. The cassette assembly 14 further includes a number of outwardly extending tubing loops interconnecting various integral passageways. The integral passageways are also interconnected to the various tubing assemblies.

Specifically, cassette assembly 14 interconnects with anticoagulant tubing 26 of the blood removal/return tubing assembly 20 and with anticoagulant tubing assembly 50. The anticoagulant tubing assembly 50 includes a spike drip chamber 52 connectable to anticoagulant and photosensitizer source 53 and a sterilizing filter 56. During use, the anticoagulant tubing assembly 50 supplies anticoagulant mixed with photosensitizer to the blood removed from donor/patient 4 to reduce or prevent any clotting in the extracorporeal tubing circuit 10. Many anticoagulants are known to the art, e.g. as disclosed in Chapter 3 of the AABB Technical Manual, 11th edition, 1993, including ACD-A, CPD, CP2D, CPDA-1, AS-1, AS-3 and AS-5, and heparin, all of which are compatible with the endogenous photosensitizers described herein.

Cassette assembly 14 also includes an interconnection with blood removal tubing of the blood removal/return tubing assembly 20. Blood passes through pressure sensors, and an inlet filter in cassette assembly 14 and thence to blood inlet tubing 62. Blood inlet tubing 62 is also interconnected with blood processing vessel 12 to provide whole blood thereto for processing.

To return separated blood components to cassette assembly 14, the blood inlet/blood component tubing assembly 60 further includes red blood cell (RBC)/plasma outlet tubing, platelet outlet tubing and plasma outlet tubing interconnected with corresponding outlet ports on blood processing vessel 12. The red blood cell (RBC)/plasma outlet tubing channels the separated red blood cell (RBC)/plasma component through cassette assembly 14 to red blood cell collection tubing assembly 70 through first decontamination system 72. The platelet outlet tubing channels separated platelets through cassette assembly 14 to platelet collection tubing assembly 80 through second decontamination system 82. The plasma outlet tubing channels separated plasma through cassette assembly 14 to plasma collection tubing assembly 90 through third decontamination system 92. After irradiation in the decontamination systems 72, 82 and 92, to activate the photosensitizer and inactivate microorganisms present, the blood components are collected in red blood cell collection bag 74, platelet collection bags 84, and plasma collection bag 94. Vent bag 104 may be used to vent gases within the system.

FIG. 7 depicts a stand-alone version of the decontamination assembly of this invention. Blood product 180 (which may be recently collected blood or blood component or stored blood) is connected to blood product line 186 which leads through pump 184 to decontamination cuvette 164. Photosensitizer reservoir 166 is connected to photosensitizer input line 168 equipped with input pump 170, and leads into blood product line 186 upstream from decontamination cuvette 164. Decontamination cuvette 164 is a photopermeable cuvette of a depth (d) and a length (l) selected to ensure decontamination. Cooling system 190 combined with temperature monitor 192 are connected with decontamination cuvette 164 for controlling the temperature of the fluid. Decontamination cuvette 164 is connected via light guide 162 to photoradiation source 160. A photoradiation enhancer 163 is placed adjacent to (either touching or spaced apart from) decontamination cuvette 164 to increase the amount of photoradiation reaching the blood product in the cuvette. Decontaminated blood product line 188 leads from decontamination cuvette 164 to decontaminated blood product collection 182.

In operation, blood product 180 is conducted into blood product line 186 where it is joined by photosensitizer from photosensitizer reservoir 166 flowing at a rate controlled by photosensitizer input pump 170 in photosensitizer input line 68 which joins blood product line 186. The flow rate in blood product line 186 is controlled by pump 184 to a rate selected to ensure decontamination in decontamination cuvette 164. Temperature monitor 192 measures the temperature of fluid in cuvette 164 and controls cooling system 190 which keeps the temperature in the cuvette within a range required for optimal operation. The blood product in decontamination cuvette 164 is irradiated by photoradiation from photoradiation source 160 conducted in light guide 162. The arrows indicate photoradiation from the end of light guide 162 propagating in the blood product inside transparent decontamination cuvette 164. Adjacent to decontamination cuvette 164 is photoradiation enhancer 163 which may be an additional source of photoradiation or a reflective surface. The arrows from photoradiation enhancer 163 pointing toward decontamination cuvette 164 indicate photoradiation from photoradiation enhancer 163 shining on the blood product material in cuvette 164. Decontaminated blood product exits decontamination cuvette 164 via decontaminated blood product line 188 and is collected at decontaminated blood product collection 182.

In a preferred embodiment using 7,8-dimethyl-10-ribityl isoalloxazine from Sigma Chemical Company as the photosensitizer, a light guide from EFOS Corporation, Williamsville, N.Y. composed of optical fibers is used. The system is capable of delivering a focused light beam with an intensity of 6,200 mW/cm$^2$ in the region of 355–380 nm. It is also possible to use interchangeable filters with the system to achieve outputs of 4,700 mW/cm$^2$ in the spectral region of 400–500 nm. In both cases, the output of light in the region of 320 nm and lower is negligible. Light guides of varying dimensions (3, 5 and 8 mm) are available with this system. The light exits the light guide tip with a 21 degree spread. The 8 mm light guide is appropriate, correctly placed, to adequately illuminate the face of the preferred decontamination cuvette which is a standard cuvette used on Cobe Spectra® disposables sets from Industrial Plastics, Inc., Forest Grove, Oreg.

The flow rate is variable and is determined by the amount of light energy intended to be delivered to the sample. The flow rate is controlled by means of a peristaltic pump from the Cole-Parmer Instrument Company, Vernon Hills, Ill. Flow rates and type of input stream may be controlled via a computer processor as is known to the art.

EXAMPLES

Example 1

Absorbance Profile of 7,8-dimethyl-10-ribityl isoalloxazine

Figure 1:
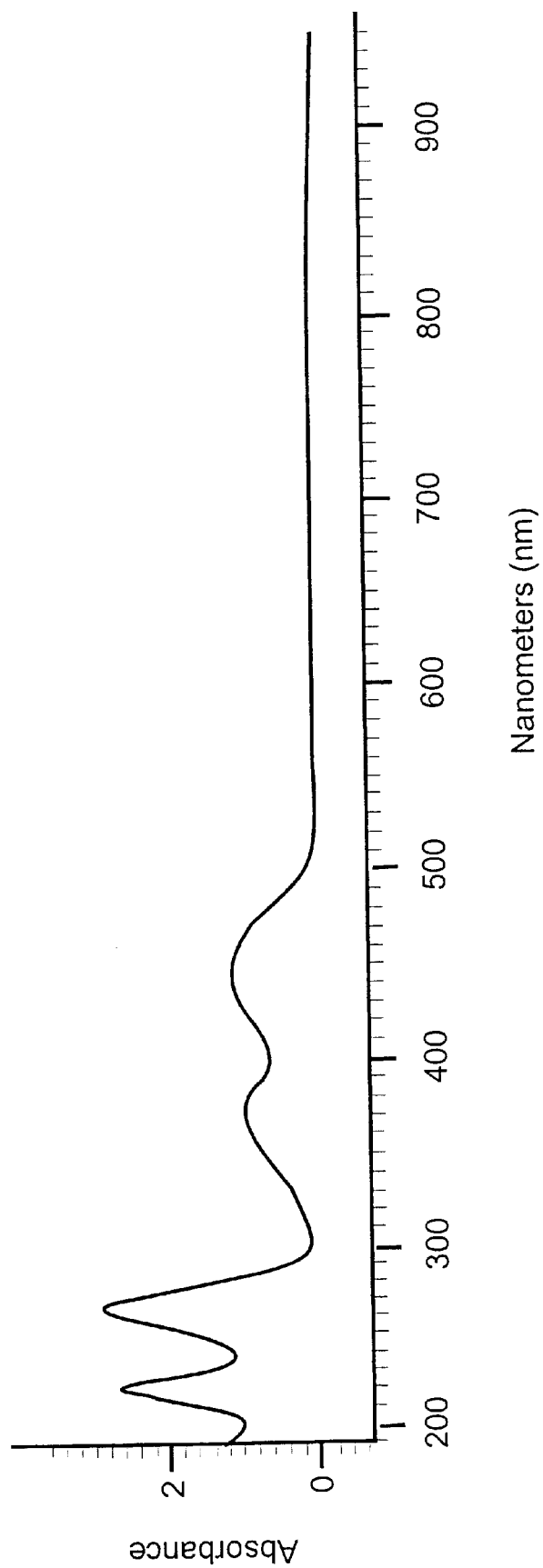
FIG. 1 depicts the riboflavin absorbance spectrum.

A sample of 7,8-dimethyl-10-ribityl isoalloxazine (98% purity) was obtained from Sigma Chemical Company. A portion of this sample was submitted for analysis using a scanning UV spectrophotometer. The range studied covered the region of 200 to 900 nm. For analysis, the sample was dissolved in distilled water. A sample spectrum from this analysis is shown in FIG. 1.

Results were consistent with those reported in the literature for the absorbance maxima and extinction coefficients for 7,8-dimethyl-10-ribityl isoalloxazine

| Literature λmax (ε) | Measured λmax (ε) |
|---|---|
| 267 (32,359) | 222 (30,965) |
|  | 265 (33,159) |
| 373 (10,471) | 373 (10,568) |
| 447 (12,303) | 445 (12,466) |

Appropriate wavelengths for irradiation are 373 and 445 nm. The extinction coefficients observed at these absorbance maxima is sufficient to ensure adequate activation of the sensitizer in solution.

Example 2

Solubility of 7,8-dimethyl-10-ribityl isoalloxazine
Solubility in Isolyte S, pH 7.4 Media The maximum solubility of 7,8-dimethyl-10-ribityl isoalloxazine in Isolyte S media was determined as follows:

7,8-dimethyl-10-ribityl isoalloxazine was mixed with Isolyte S until a precipitate was formed. The mixture was agitated at room temperature for one hour and vortex mixed to ensure complete dissolution of the suspended material. Additional 7,8-dimethyl-10-ribityl isoalloxazine was added until a solid suspension remained despite additional vortex mixing. This suspension was then centrifuged to remove undissolved material. The supernatant from this preparation was removed and analyzed using a spectrophotometer. The absorbance values of the solution were determined at 447 nm and 373 nm. From the extinction coefficients that were determined previously, it was possible to estimate the concentration of the saturated solution.

Concentration (373)=110 μM=42 μg/mL

Concentration (447)=109 μM=40.9 μg/mL

Solubility in ACD Anticoagulant

The same procedure described above was repeated using ACD Anticoagulant. The values obtained from these measurements were as follows:

Concentration (373)=166 μM=63 μg/mL

Concentration (447)=160 μM=60.3 μg/mL

The values obtained from these studies indicate an upper limit of solubility of the compound that may be expected.

Example 3

Figure 3:
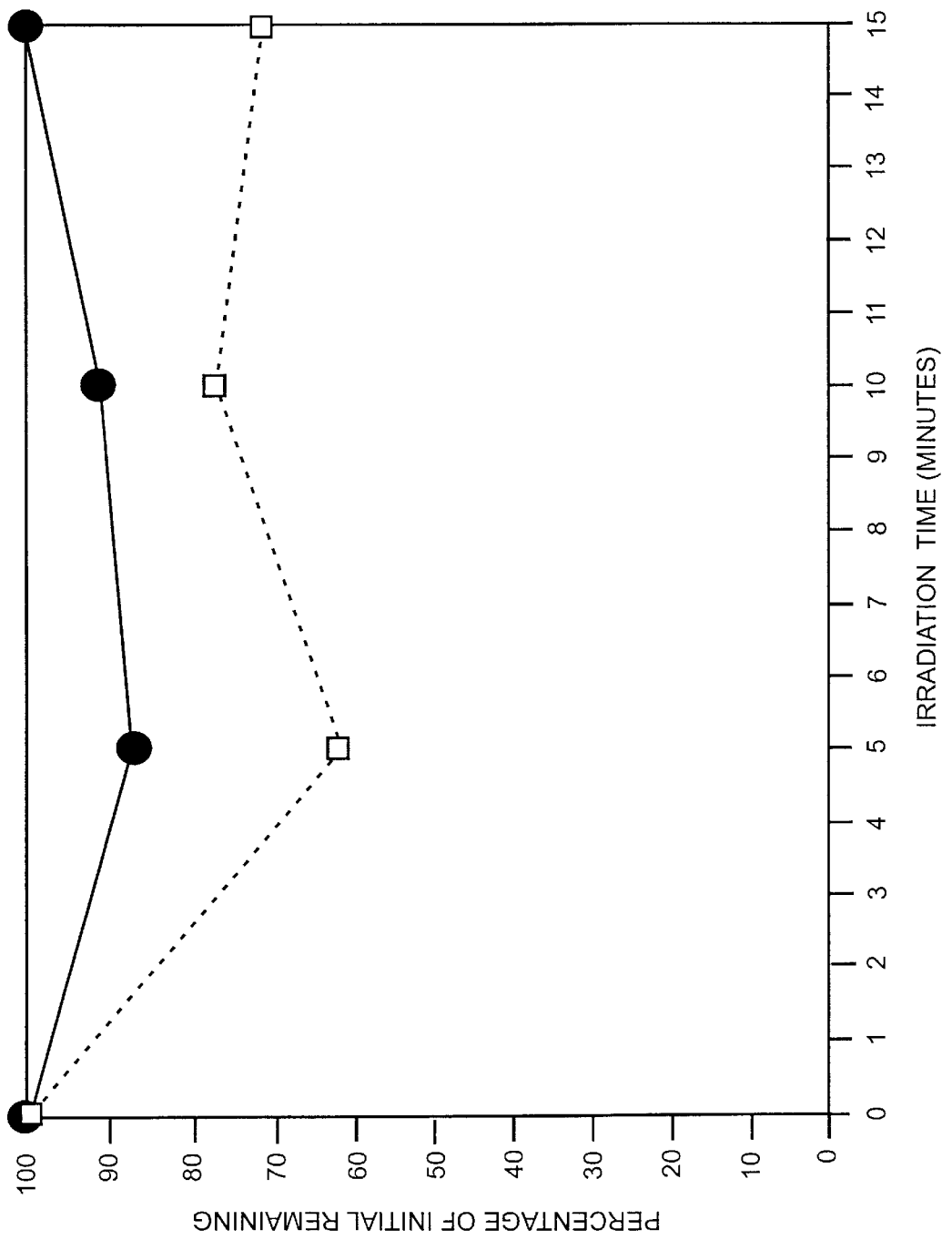
FIG. 3 depicts photodecomposition over time of riboflavin in anticoagulant Acid Citrate Dextrose (ACD) solution. The solid line with circles indicates percent of initial riboflavin remaining at 373 nm. The dotted line with squares indicates percent of initial riboflavin remaining at 447 nm.

Photodecomposition of 7,8-dimethyl-10-ribityl isoalloxazine in Aqueous Media A solution of 7,8-dimethyl-10-ribityl isoalloxazine in Sigma ACD-A was prepared at a concentration of 63 μg/mL. This preparation was taken up into a glass pipette and placed in the path of a UV light source (365 nm λmax with filters to remove light below 320 nm). The suspension was irradiated for specific intervals at which aliquots were removed for spectroscopic analysis. The absorbance of the dissolved 7,8-dimethyl-10-ribityl isoalloxazine was monitored at 373 and 447 nm at each time interval. The results are depicted in FIG. 3 and Table 1.

TABLE 1

Photodecomposition of 7,8-dimethyl-10-ribityl isoalloxazine
Upon Exposure to UV Light (365 nm) in Acid Solution

| Irradiation Time | % of Initial, 373 nm | % of Initial, 447 nm |
|---|---|---|
| 0 | 100 | 100 |
| 5 | 87.3 | 61.6 |
| 10 | 90.5 | 76.6 |
| 15 | 100 | 70 |

The absorption profile for the solution at 373 nm indicates that no significant decomposition of the reagent occurred over the entire irradiation period. The absorbance of light at this wavelength corresponds to n-π* electronic transitions.

The absence of a decrease in the intensity of this peak over time indicates that the ring structure of the molecule is intact despite prolonged irradiation under these conditions. The absorbance of the molecule at 447 nm is due to $\pi$-$\pi$* electronic state transitions. The decrease in the absorbance of the molecule at this wavelength with increasing irradiation times is indicative of subtle alterations in the resonance structure of the molecule. This change is most likely due to the loss of ribose from the ring structure of the 7,8-dimethyl-10-ribityl isoalloxazine backbone and the formation of lumiflavine as a result. These changes are consistent with literature reports on the behavior of the molecule upon irradiation with UV light.

The apparent lack of decomposition of the ring structure of the molecule is in stark contrast to observations with psoralen based compounds under similar conditions. During irradiation, a significant fluorescence of the molecule in solution was observed. This behavior of the molecule is consistent with the resonance features of the ring structure and provides a means for the dissipation of energy in the excited state molecule in a non-destructive fashion.

Example 4

Flow System Concept Evaluation

Light Transmission Properties of Existing Spectra Cuvette

The existing Spectra cuvette is composed of polycarbonate. The light transmission properties of this cuvette were measured at 373 and 447 nm by placing the cuvette in the light path of a UV spectrophotometer. The values obtained were as follows:

| Wavelength of Light | % Transmittance |
|---|---|
| 373 nm | 66% |
| 447 nm | 80% |

Figure 4:
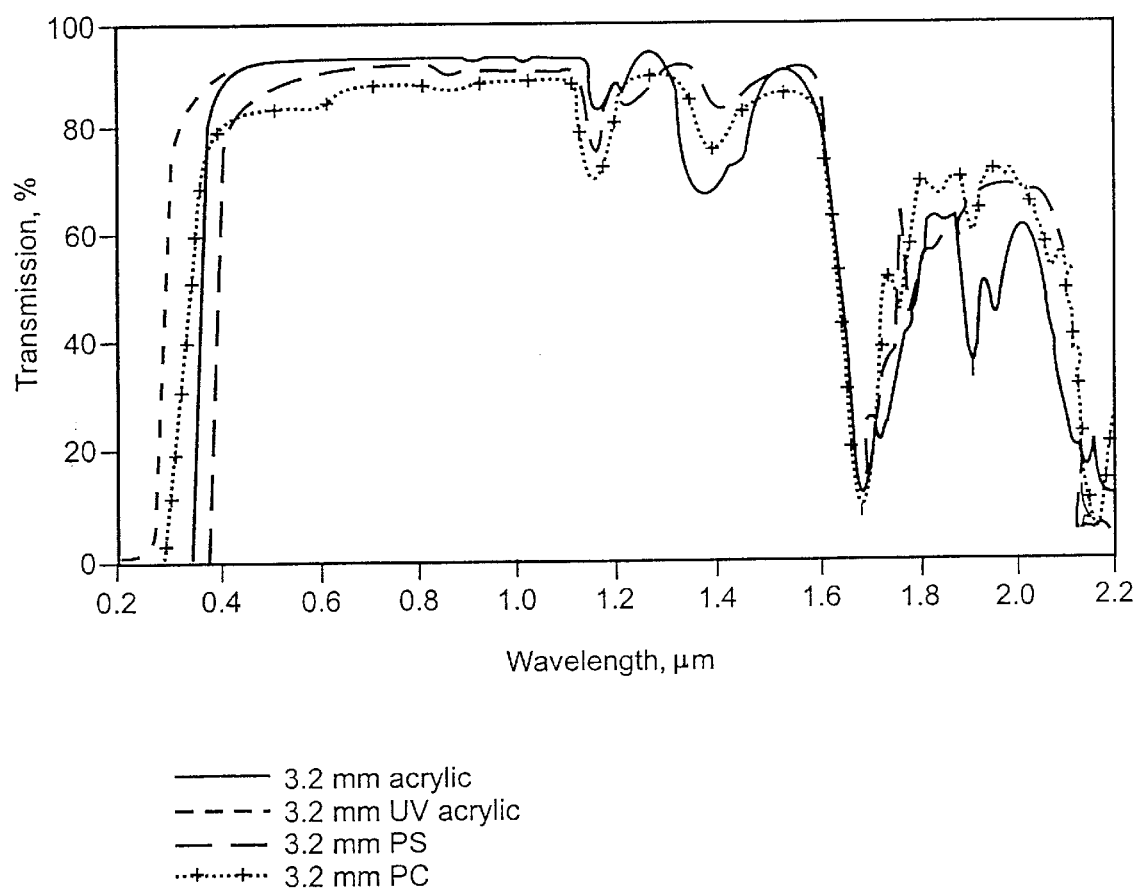
FIG. 4 depicts the transmission profile of various plastic cuvettes as a function of wavelength. The solid line represent a 3.2 mm acrylic cuvette. The dotted line (---) represents a 3.2 mm UV acrylic cuvette. The dashed line (——) represents a 3.2 mm polystyrene (PS) cuvette, and the crossed line indicates a 3.2 mm polycarbonate (PC) cuvette.
Figure 5:
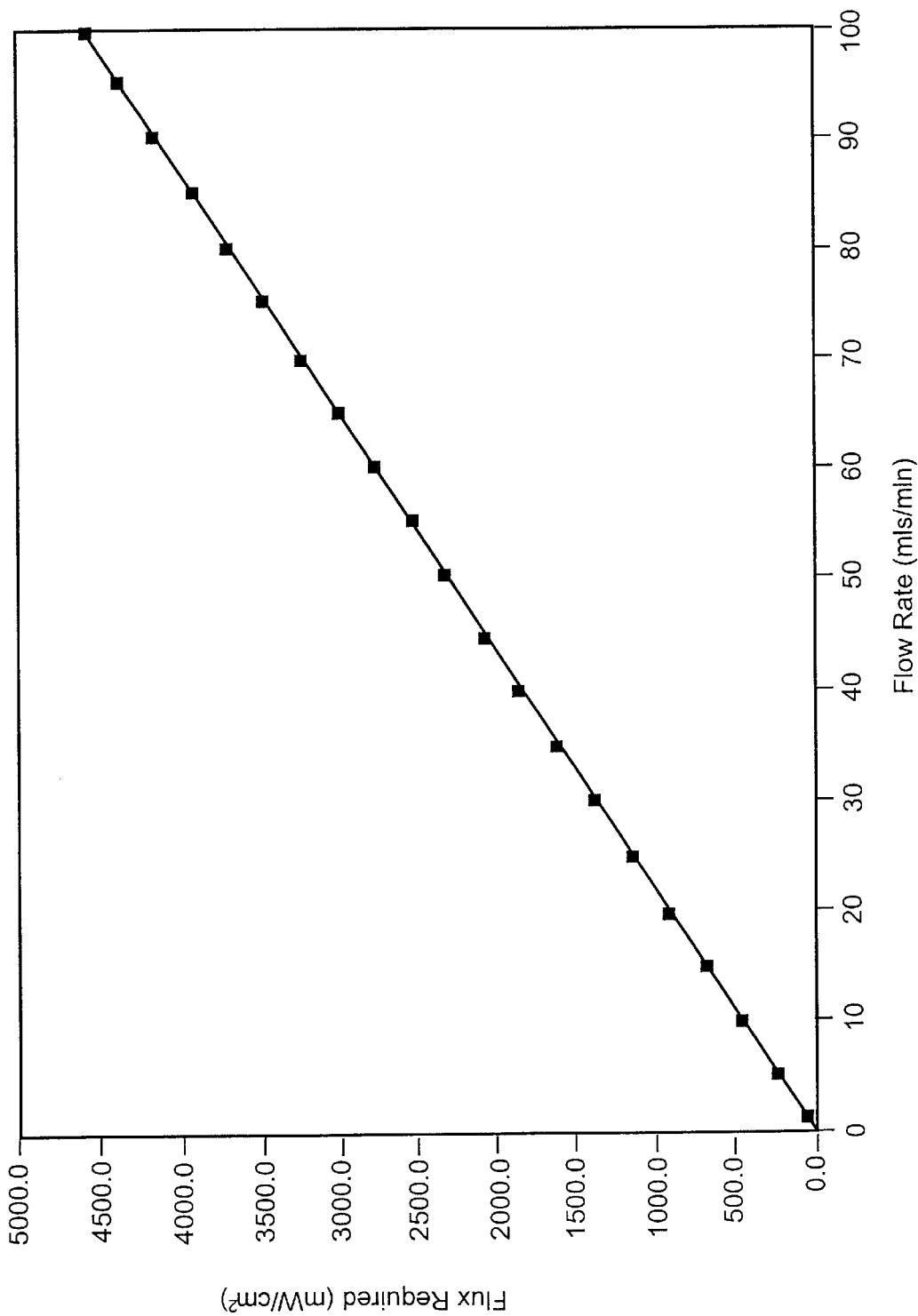
FIG. 5 depicts the light flux required in mW per $cm^2$ as a function of flow rate, i.e. the flux required to deliver one joule/$cm^2$ to a sample in the cuvette.

These results are consistent with those reported in the literature for polycarbonate plastics (see FIG. 4). The literature values indicate a steep shoulder for the transmission of light through polycarbonates in the region of 300 nm. For the region above 350 nm, the light transmission properties are adequate for this application.

Light Flux Requirements Calculated as a Function of Flow Rates

In order for a flow system to be feasible, the sample must be provided with an adequate flux of light during its presence in the beam path. If the proposed Spectra cuvette were to serve this purpose, then it is possible to estimate the light flux requirements as a function of flow rates through the cuvette as follows:

The volume of solution present in the irradiation zone of the cuvette is ca. 0.375 mls. The transit time for a cell in this region of the cuvette can be determined from the following equation:

$$T = \frac{\text{Volume of Cuvette (mls)}}{\text{Flow Rate (mls/min)}}$$

At 100 mls per minute, the transit time (T) would be 0.00375 mm=0.225 seconds.

The energy to which a sample is exposed is dependent on the flux according to the following equation:

$$\text{Energy}(E, \text{Joules/cm}^2) = \frac{\text{Flux}(\phi, \text{mW/cm}^2) * \text{Time}(T, \text{sec.})}{1000}$$

If we assume that 1 Joule/cm$^2$) is required to activate the sensitizer adequately and the transit time (T) is 0.22 seconds (i.e., flow rate of 100 mls/min through the cuvette), then the required Flux during the sample's transit through the cuvette is 4,545 mW/cm$^2$. A graph depicting the relationship of the required flux from the light source to flow rates through the cuvette is provided in FIG. 5.

These results indicate that, for a flow system to operate properly, UV sources with outputs in the region of Watts/cm$^2$ are required.

Figure 2:
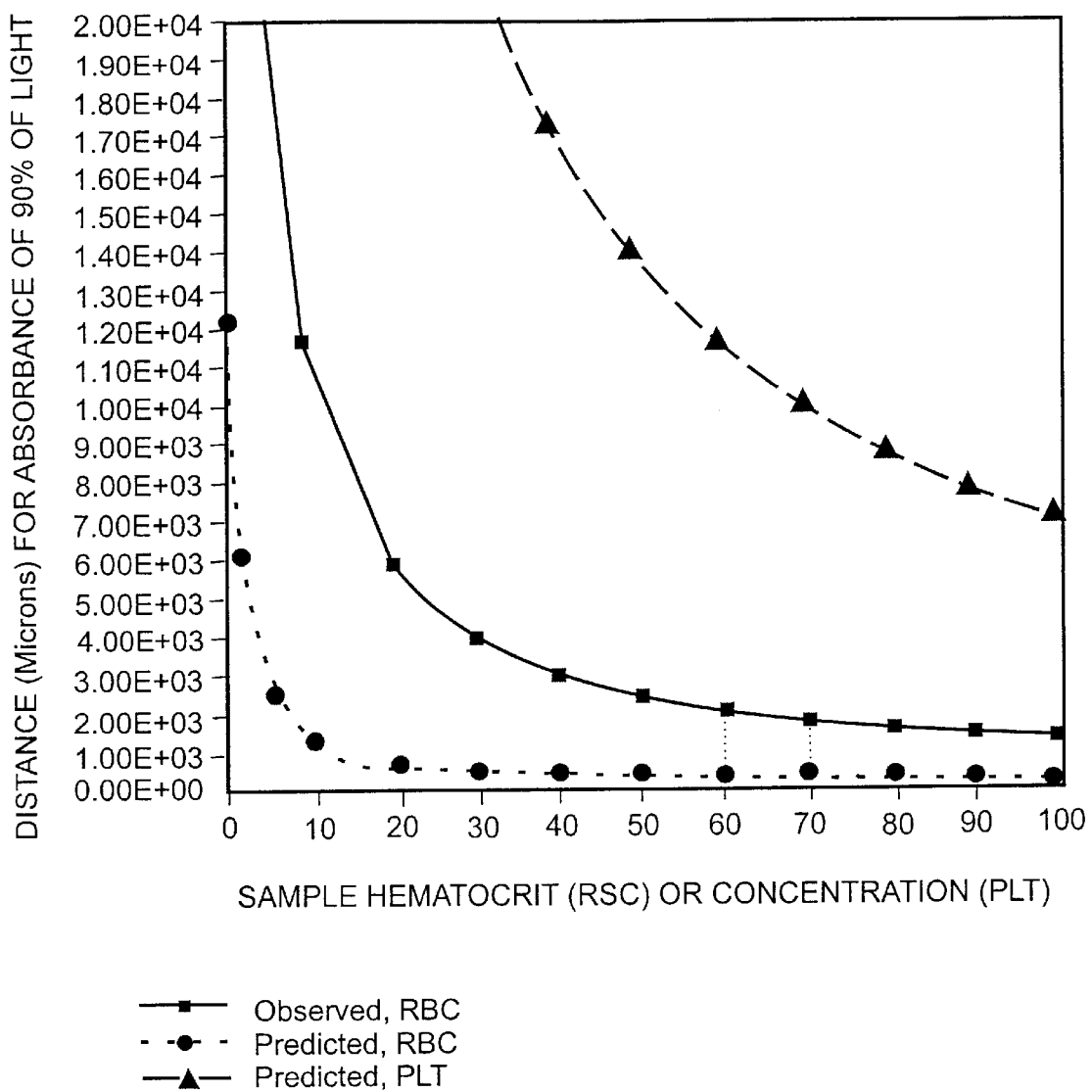
FIG. 2 depicts a correlation of light absorbance and hematocrit observed and predicted for red blood cells, and predicted for platelets.

FIG. 2 shows how absorbance should vary with hematocrit for platelets.

Example 5

Absorbance of Red Blood Cells

In order to evaluate the extent to which UV light can penetrate a red cell sample and the effects of sample thickness and hematocrit on the extent of light penetration, several preliminary experiments were carried out using chemical actinometry, a method for determining the actual amount of light intensity emanating from a source by measuring the ability and extent to which absorbed light can effect a chemical reaction. For these studies, a ferrioxalate solution was utilized in order to measure the source intensity relative to that observed for water. Details of the chemical reaction and the methods utilized for sample preparation are as taught in Gordon, A. J. and Ford, R. A. (1972), "The Chemist's Companion: A Handbook of Practical Data, Techniques and References" (John Wiley & Sons), pp. 362–368.

Samples of iron (III) oxalate were prepared in the test material (water or blood product at varying red cell hematocrits) at a concentration of 0.15 M. These samples were then loaded into a standard Spectra cuvette and placed in the irradiation assembly. Samples were exposed for pre-determined time intervals corresponding to the desired energy dose level (1 J/cm$^2$). The samples were then removed and the amount of conversion of Fe$^{3+}$ to Fe$^{2+}$ was determined by reading the absorbance of the test article in a 1,10-phenanthroline solution at 510 nm as described in Gordon, A. J. and Ford, R. A., supra. Higher absorbance values are indicative of greater light penetration into the sample. The absorbance value observed for water after exposure to 1 J/cm$^2$ UV radiation was used as the 100% Transmittance level. All values for red cell samples were determined relative to this standard.

TABLE 2

Absorbance Readings After Exposure of Samples to 1 J/cm$^2$ UVA Light. All Average Values Represent the Mean of 6 Experiments. % Transmittance Values Are Calculated Relative to Water Samples.

| Absorbance at 510 nm | Average | Standard Deviation | % Transmittance | Standard Deviation |
|---|---|---|---|---|
| Water | 2.40 | 0.04 | 100 | 0.0 |
| RBC, 1.3% Hematocrit | 2.40 | 0.10 | 99.9 | 4.8 |
| RBC, 3.7% Hematocrit | 1.46 | 0.38 | 60.6 | 15.4 |
| RBC, 5.07% Hematocrit | 0.20 | 0.26 | 8.3 | 10.8 |

TABLE 2-continued

Absorbance Readings After Exposure of Samples to 1 J/cm² UVA Light.
All Average Values Represent the Mean of 6 Experiments.
% Transmittance Values Are Calculated Relative to Water Samples.

| Absorbance at 510 nm | Average | Standard Deviation | % Transmittance | Standard Deviation |
|---|---|---|---|---|
| RBC, 6.0% Hematocrit | 0.13 | 0.09 | 5.2 | 3.9 |
| RBC, 10.2% Hematocrit | 0.23 | 0.19 | 9.7 | 7.9 |
| RBC, 16.3% Hematocrit | 0.25 | 0.11 | 10.4 | 4.6 |
| RBC, 21.8% Hematocrit | 0.09 | 0.06 | 3.6 | 2.6 |
| RBC, 80.2% Hematocrit | 0.01 | 0.11 | 0.3 | 4.4 |

Using these values, it is possible to calculate the penetration depth of UV light by using Beer's Law ($A = \epsilon b C$—Formula I above).

From Lambert's Law, $$\text{Absorbance} = \text{Log}(1/\text{Transmittance})$$

If we let the concentration (C) be equal to the hematocrit of the sample, and since b=0.3 cm (the path length of the Spectra cuvette), then it is possible to determine a pseudo-extinction coefficient for the samples ($\epsilon'$) by plotting the absorbance values for the red cell samples versus the product of the hematocrit times the path length. The extinction coefficient for the samples is represented by the slope of this line.

TABLE 3

Determination of Extinction Coefficient for Red Cell Samples.

| T | B | HCT | B*HCT | Absorbance log (1/T) |
|---|---|---|---|---|
| 0.995 | 0.3 | 1.3 | 0.39 | 0.002 |
| 0.606 | 0.3 | 3.7 | 1.11 | 0.218 |
| 0.0525 | 0.3 | 6 | 1.8 | 1.280 |
| 0.097 | 0.3 | 10.2 | 3.06 | 1.013 |
| 0.104 | 0.3 | 16.3 | 4.89 | 0.983 |
| 0.036 | 0.3 | 21.8 | 6.54 | 1.444 |
| 0.0033 | 0.3 | 80.2 | 24.06 | 2.481 |

Using the values obtained as described above, it was possible to determine a pseudo-extinction coefficient for these samples to be 0.08661.

The value for the extinction coefficient permits calculation of the penetration distance of UV light into red cell samples as a function of the sample hematocrit. For this estimation, the penetration depth of the sample in which 90% of the incident light would be absorbed was determined using the following equation:

$$A = \epsilon b C$$

A=1 (90% Absorbance of Incident Light), E=0.08661, C=Sample hematocrit, b=Path Length.

The values determined using actinometry were compared to those which were calculated previously using estimates taken from UV Spectrophotometric measurements of light absorbance in red cell and platelet samples.

FIG. 2 shows how absorbance and distance from the light source varies for red blood cells, comparing predicted with observed values. These results indicate that, for samples at hematocrits in the region of 80%, it is possible, using the preferred configuration of this invention, to get light into the sample to a depth of 0.14 cm. This represents a flow path width that is less than half the width of the current Spectra cuvette.

Example 6

Effects of Virus Inactivation Treatment on Platelet In Vitro Parameters

Effects of virus inactivation treatment on platelet in vitro parameters were evaluated. Platelet preparations were treated with 7,8-dimethyl-10-ribityl isoalloxazine in combination with UV light. Various in vitro parameters were used as monitors of platelet function in order to determine the extent of changes induced by the treatment conditions. Factors such as energy level of UV light exposure, dose of 7,8-dimethyl-10-ribityl isoalloxazine used, and sample processing conditions were examined for their impact on platelet quality post-treatment. Results from this study are used to establish an appropriate treatment window for inactivation of HIV-1 without compromising platelet function.

Samples were prepared with three different concentrations of 7,8-dimethyl-10-ribityl isoalloxazine. Platelets obtained from a standard Spectra LRS collection were used for these studies.

Starting samples were centrifuged to concentrate the platelet pellet. The pellet was resuspended in a 70:30 (Isolyte S, pH 7.4; McGaw, Inc. Media:Plasma) solution. 7,8-dimethyl-10-ribityl isoalloxazine at the specified concentration, was present in the plasma:media mixture. The platelet suspension was then passed through a UV irradiation chamber at one of three specified flow rates. The flow rates were directly correlated to the energy level of exposure for the cells/media mixture which passes through the irradiation chamber. After flowing through the irradiation chamber, samples were stored in a citrate plasticized sampler bag for subsequent analysis.

Following irradiation, in vitro measurements of platelet function, including hypotonic shock response (HSR), GMP-140 expression, pH, pCO$_2$, pO$_2$, platelet swirl, and cell count, were evaluated in order to determine the effects of the treatment protocol on cell quality.

Platelet quality factor (Q) was monitored as a function of irradiation conditions (sensitizer concentration and flow rates/Energy levels). The quality factor includes parameters such as HSR response, GMP-140 activation, etc. The flow rates that are studied can be related to the Energy of exposure as follows:

$$\text{Transit Time}(T, \text{sec}) = \text{Exposure Time} = \frac{0.375 \text{ mls}}{(F_r/60)}$$

$F_r$=Flow Rate (mls/min)
0.375 mls=Cuvette Volume (mls)

$$\therefore T(\text{sec}) = \frac{22}{F_r}$$

$$\text{Energy(Joules/cm}^2) = \frac{\text{Flux}(\phi, \text{mW/cm}^2) * T(\text{sec})}{1000}$$

$$E = \frac{\phi * 0.022}{F_r}$$

FIG. 2 shows how absorbance should vary with hematocrit for platelets.

The effect of energy of UV exposure and concentration of 7,8-dimethyl-10-ribityl isoalloxazine on the stability and viability of treated platelets was evaluated. Three energy levels and three concentration levels were evaluated as follows:

| Energy Levels: | 1,5,9 J/cm$^{2*}$ |
|---|---|
| 7,8-dimethyl-10-ribityl isoalloxazine Concentrations: | 1, 50, 100 $\mu$M** |

TABLE 4

Energy Exposure Levels as a Function of Flow Rate Through the Irradiation Chamber

| Energy Delivered (J/cm$^2$) | Flow Rate (mls/min) | Time to process 20 mls (minutes) |
|---|---|---|
| 1 | 16.90 | 1.18 |
| 2 | 8.45 | 2.37 |
| 3 | 5.83 | 3.55 |
| 4 | 4.22 | 4.73 |
| 5 | 3.38 | 5.92 |
| 6 | 2.82 | 7.10 |
| 7 | 2.41 | 8.29 |
| 8 | 2.11 | 9.47 |
| 9 | 1.88 | 10.65 |
| 10 | 1.69 | 11.84 |

Flux = 3640 mW/cm$^2$; chamber volume = 0.117 mls.

Values for treated samples were compared to control groups. The control samples included the following:

Untreated Sample in Plasma (Historical Control)
+Flow-UV-7,8-dimethyl-10-ribityl isoalloxazine
Procedure A normal donor platelet apheresis product was obtained from an AABB accredited blood banking facility. The sample was collected using standard Spectra LRS procedures. All manipulations or procedures described below were performed with standard laboratory safety procedures and methods. The unit number and blood type were recorded. All samples were used within 24 hours of collection. Aseptic procedure was followed for all sample transfers and processing steps.

The sample was transferred to a 500 mls PVC transfer pack and centrifuged at 5000xg for five minutes to pack the platelets. Plasma was then removed from the platelet pellet using a standard plasma press. The plasma was retained for further use. The plasma removed from the cell pellet was then mixed with a stock solution of Isolyte S, pH 7.4; McGaw, Inc. This stock solution of media was prepared by adding a pre-determined amount of 7,8-dimethyl-10-ribityl isoalloxazine to Isolyte S to provide final concentrations of 1.43, 71.4, and 143 $\mu$M. Following addition of 7,8-dimethyl-10-ribityl isoalloxazine the stock solution was filtered through a 0.22 $\mu$M sterile filter. The stock solution was then mixed with autologous plasma in a 70:30 (v:v) ratio to provide final 7,8-dimethyl-10-ribityl isoalloxazine concentrations of 1, 50, and 100 $\mu$M respectively. During preparation of the 7,8-dimethyl-10-ribityl isoalloxazine stock solutions, care was taken to avoid exposure to light. Samples were prepared according as follows:

| 1 $\mu$M | 2 samples |
|---|---|
| 100 $\mu$M | 2 samples |
| 50 $\mu$M | 1 sample |

The platelet pellet was then resuspended in the plasma-:media mixture to the original volume of the starting sample. The sample was connected to a flow apparatus comprising a container for cells and photosensitizer, a container for media, said containers being connected via valved lines to a single line for mixed cells/sensitizer and media equipped with a pump. Mixed cells/sensitizer and media were flowed into a cuvette held in a holder with a mirrored wall, irradiated by a light source. This irradiation chamber was equipped with a temperature probe. After passing through the cuvette, fluid was collected in a product bag.

The tubing set was initially primed with Isolyte S media. Five minutes prior to the start of the test sample flow, the light source was activated. Temperature was monitored during this interval and kept lower than 32° C. in the irradiation chamber.

The flow rate for the sample through the irradiation chamber was determined by the chart of Table 4. Flow rates which provide total irradiation energy levels of 1, 5 and 9 J/cm$^2$ were utilized according to the following testing matrix:

Sample Run #1: 7,8-dimethyl-10-ribityl isoalloxazine Concentration=1 $\mu$M
  A. +7,8-dimethyl-10-ribityl isoalloxazine+1 J/cm$^2$
  B. +7,8-dimethyl-10-ribityl isoalloxazine+9 J/cm$^2$
Sample Run #2: 7,8-dimethyl-10-ribityl isoalloxazine=100 $\mu$M
  A. +7,8-dimethyl-10-ribityl isoalloxazine+1 J/cm$^2$
  B. +7,8-dimethyl-10-ribityl isoalloxazine+9 J/cm$^2$
Sample Run #3: 7,8-dimethyl-10-ribityl isoalloxazine=50 $\mu$M
  A. +7,8-dimethyl-10-ribityl isoalloxazine+5 J/cm$^2$
Sample Run #4: Control Sample, 7,8-dimethyl-10-ribityl isoalloxazine=0 $\mu$M
  A. +Flow-UV-7,8-dimethyl-10-ribityl isoalloxazine All samples were identified by the run number and sample letter designation corresponding to treatment condition (i.e., 1A). Each sample set was run for a total of 2 replicates. The order in which samples were treated was determined by assignment according to a random number generator.

A sample volume of 20 mls per run condition was collected for each sample. These samples were collected into citrate plasticized sampling bags (53 mls total volume) and stored for analysis. The temperature of the sample and the irradiation chamber was noted at the start, mid-point, and end of each run.

An initial aliquot from each preparation was removed post-treatment for analysis. Parameters for analysis included cell count, pH, pCO$_2$, pO$_2$, platelet swirl, HSR, and GMP-140 analysis. The remaining portion of the sample was placed in an end-over-end platelet agitator in a +22 incubator and stored for five days post-treatment. On day 5, a second aliquot was removed and analyzed for the same in vitro parameters.

The following equipment was used: Nikon Labophot microscope; Serono-Baker System 9000 Hematology Analyzer; analytical balance; platelet incubator (+22 Celsius) and rotator; laboratory refrigerator (+4 Celsius); Mistral 3000i Centrifuge; Corning Blood Gas Analyzer; Becton-Dickinson FACSCALIBUR Flow Cytometer, UV irradiation chamber; UV radiometer (UVX Radiometer, UVP, Inc.); EFOS Ultracure 100SS Plus (365 nm maximum output and 340 nm bandpass filters); and temperature probe (thermocouple).

Results for each set of test variables were compared for the defined conditions of energy of exposure and concentration of 7,8-dimethyl-10-ribityl isoalloxazine. Direct comparison to the untreated control sample was made and significant differences defined by a probability p>0.05 from a paired, one-tailed, Student's T-Test analysis.

The results from these studies were summarized as follows:

1. At sensitizer concentrations in excess of 10 µM and platelet concentrations above 1.5E+06/mL, there was a drop in sample pH by day 2. The pH declined steadily beyond day 2 of storage reaching unacceptable levels (<6.5) by day 3 of storage. All other in vitro parameters followed the pattern observed with sample pH.
2. This decrease in sample pH occurred regardless of whether or not the sample was exposed to UV light.
3. At platelet concentrations of 5.4E+05/mL, there was no drop in sample pH after extended storage at any sensitizer concentration studied up to 100 µM.
4. At sensitizer concentrations up to 10 µM, platelet concentrations above 1.5E+06/mL, and UVA levels up to 10 J/cm$^2$, measured platelet properties were comparable to control, untreated cells. These remained comparable to control levels after five or more days of storage post-treatment.

These studies on platelet function post-treatment provided a clear window in which cell properties were maintained at levels comparable to untreated cells. The results also indicated that by varying the storage or treatment conditions for the cells this window can be expanded. The observed effect of 7,8-dimethyl-10-ribityl isoalloxazine with or without UV light on sample pH suggests a metabolic effect of this additive which may be moderated by changes in the storage or processing conditions of the samples.

Example 7

Measurements of Shear Stresses on Red Cells As a Function of Flow Rate and Sample Hematocrit The low levels of UV light penetration into red cell samples at high hematocrits raised the need to understand the effects of passing red cells through narrow openings in the light path. Reduction in sample thickness in the light path should increase delivery of UV dose at high sample hematocrits. In order to confirm this approach, several pressure drop measurements were undertaken using openings of varying dimensions. A pressure gauge was placed in line with a peristaltic pump both upstream and downstream from the narrowed openings. Whole blood of varying hematocrits was passed through the openings at controlled flow rates. Differences in the pressure readings at both locations permitted direct measurement of the pressure drop across the opening. Using this value and the dimensions of the opening, it was possible to determine the shear stress experienced by the red cells as they passed through the narrowed cell using the following equation:

$$\Delta P = \frac{8 \mu l Q}{g d^3 w} \quad \text{Pressure Drop}$$

$$\tau_w = \frac{4 \mu Q}{g w d^2} \quad \text{Shear Stress}$$

For blood,

µ=Viscosity=0.0125/(1-Hematocrit)

g=gravitational constant=981

Q=Flow Rate=mls/sec l, w, d=Dimensions of opening in cm

TABLE 5

Measurement of Shear Stress on Red Cells As Functions of Flow Rate and Sample Hematocrit

|  |  | 0.08 × 0.008 | Dpmeas (dynes/cm$^2$) | 0.08 × 0010 | Dpmeas (dynes/cm$^2$) | 0.08 × 0012 | Dpmeas (dynes/cm$^2$) |
|---|---|---|---|---|---|---|---|
| 41% HCT | Q = 3.38 | 1.5 | 95.9 | 1.0 | 77.6 | 0.0 | 0.0 |
| 64% HCT | Q = 3.38 | 4.0 | 255.8 | 3.0 | 232.9 | 2.0 | 182.1 |
| 41% HCT | Q = 16.9 | 9.7 | 618.4 | 7.0 | 543.4 | 4.7 | 425.3 |
| 61% HCT | Q = 16.9 | 20.7 | 1321.9 | 12.3 | 957.2 | 8.7 | 789.6 |
|  |  | 0.10 × 0.008 | Dpmeas (dynes/cm$^2$) | 0.1 × 0010 | Dpmeas (dynes/cm$^2$) | 0.1 × 0012 | Dpmeas (dynes/cm$^2$) |
| 41% HCT | Q = 3.38 | 2.0 | 93.7 | 1.0 | 60.3 | 1.0 | 73.5 |
| 64% HCT | Q = 3.38 | 4.5 | 210.8 | 3.0 | 180.9 | 2.0 | 146.9 |
| 41% HCT | Q = 16.9 | 12.7 | 593.6 | 7.0 | 422.1 | 4.7 | 343.0 |
| 61% HCT | Q = 16.9 | 23.3 | 1093.0 | 14.7 | 884.6 | 12.0 | 881.4 |
|  |  | 0.15 × 0.008 | Dpmeas (dynes/cm$^2$) | 0.15 × 0010 | Dpmeas (dynes/cm$^2$) | 0.15 × 0012 | Dpmeas (dynes/cm$^2$) |
| 41% HCT | Q = 3.38 | 3.0 | 97.4 | 1.2 | 49.2 | 1.0 | 49.0 |
| 64% HCT | Q = 3.38 | 6.5 | 211.0 | 3.5 | 143.5 | 2.0 | 97.9 |
| 41% HCT | Q = 16.9 | 15.3 | 497.7 | 8.3 | 341.6 | 5.7 | 277.6 |
| 61% HCT | Q = 16.9 | 35.7 | 1158.1 | 18.0 | 738.1 | 12.7 | 620.4 |

In previous experiments, it was determined that shear stresses of 1,000–2,000 dynes/cm$^2$ for intervals of 1–10 minutes or levels of 5,000–7,000 dynes/cm$^2$ for intervals of approximately 10 msec were sufficient to induce red cell hemolysis. Only in the case of the highest sample hematocrit (61%) and highest flow rate (16.9) did values exceed 1,000 dynes/cm$^2$. This occurred only for openings of the narrowest width (0.008 inches).

Values for the light penetration depth using the proposed configuration indicate that delivery in sufficient UV energy to drive virus inactivation processes is achievable even for samples with high hematocrits.

Results from shear stress analysis on red cell samples subjected to flow indicate that flow path dimensions may be significantly reduced and high flow rates maintained without risking red cell hemolysis.

It will be readily understood by those skilled in the art that the foregoing description has been for purposes of illustration only and that a number of changes may be made without departing from the scope of the invention. For example, other photosensitizers than those mentioned may be used, preferably photosensitizers which bind to nucleic acid and thereby keep it from replicating, and more preferably those which are not toxic and do not have toxic breakdown products. In addition, equivalent structures to those described herein for constructing a flow-through system for decontamination of fluids using photosensitizers may be readily devised without undue experimentation by those skilled in the art following the teachings hereof.

What is claimed is:

1. A method for decontamination of a fluid, by inactivation of microorganisms therein, sufficiently effective such that said fluid can be administered to a patient, said fluid also containing a component selected from the group consisting of biologically active protein, blood, and blood constituents, without destroying the biological activity of such component, said method comprising:
   (a) adding an effective, non-toxic amount of an endogenous alloxazine or isoalloxazine photosensitizer to said fluid;
   (b) exposing the fluid of step (a) to photoradiation sufficient to activate the endogenous photosensitizer;
   (c) allowing said activated endogenous photosensitizer to inactivate said microorganisms.

2. The method of claim 1 wherein said endogenous photosensitizer is a nucleic-acid-targeted non-toxic, photoactivatable compound which does not produce toxic photolytic breakdown products.

3. The method of claim 1 wherein said endogenous photosensitizer is 7,8-dimethyl-10-ribityl isoalloxazine.

4. The method of claim 1 wherein said photoradiation is done using light in the visible spectrum.

5. The method of claim 1 wherein said photoradiation is done using light in the ultraviolet spectrum.

6. The method of claim 1 wherein said fluid of step (a) is flowed past a source of photoradiation at a rate and depth selected to ensure penetration of the photoradiation through the fluid and inactivation of the microorganisms.

7. The method of claim 1 wherein said fluid comprises blood constituents.

8. The method of claim 1 wherein said fluid is whole blood.

9. The method of claim 1 wherein said fluid is a separated blood product.

10. The method of claim 1 wherein said microorganisms are viruses.

11. The method of claim 1 wherein said endogenous photosensitizer is added to anticoagulant and said anticoagulant is added to said fluid.

12. The method of claim 1 wherein said photosensitizer is capable of inactivating microorganisms in the absence of oxygen.

13. The method of claim 1 wherein said photosensitizer is capable of inactivating microorganisms at pH about 7.4.

14. The method of claim 1 wherein said photosensitizer is capable of inactivating microorganisms in the presence of plasma, cells or blood components.

15. The method of claim 1 wherein said photosensitizer inactivates microorganisms present in human blood.

16. A fluid comprising biologically active protein, blood or blood constituents and inactivated microorganisms and endogenous photosensitizer or photoproduct thereof, made by the method of claim 1.

17. A blood product comprising inactivated microorganisms and endogenous photosensitizer or photoproduct thereof, made by the method of claim 1.

18. An extracorporeal method for decontamination of a fluid, by inactivation of microorganisms therein, sufficiently effective such that said fluid can be administered to a patient, said fluid also containing a component selected from the group consisting of biologically active protein, blood, and blood constituents, without destroying the biological activity of such component, said method comprising:
   (a) adding to said fluid an effective, non-toxic amount of an endogenous alloxazine or isoalloxazine photosensitizer which inactivates microorganisms in the presence of albumin;
   (b) exposing the fluid of step (a) to photoradiation sufficient to activate the endogenous photosensitizer; and
   (c) allowing said activated endogenous photosensitizer to inactivate said microorganisms.

* * * * *

UNITED STATES PATENT AND TRADEMARK OFFICE
CERTIFICATE OF CORRECTION

PATENT NO. : 6,258,577 B1  Page 1 of 1
DATED : July 10, 2001
INVENTOR(S) : Goodrich, Jr. et al.

It is certified that error appears in the above-identified patent and that said Letters Patent is hereby corrected as shown below:

Column 19,
Line 10, immediately above Table 4, please insert -- *Levels of total energy exposure were determined by the flow rate of the suspension through the irradiation chamber in accordance with the conversion chart of Table 4. **Since the media is diluted 70:30 (Media:Plasma) the stock concentration of 7,8-dimethyl-10-ribityl isoalloxazine in media alone prior to mixing with the plasma was adjusted appropriately. This required starting concentrations in Isolyte S of 1.43, 71.4, and 143 $\mu$M. --

Signed and Sealed this

Twenty-first Day of January, 2003

JAMES E. ROGAN
*Director of the United States Patent and Trademark Office*